United States Patent
Johnson

(10) Patent No.: US 8,676,603 B2
(45) Date of Patent: *Mar. 18, 2014

(54) SYSTEM AND METHOD FOR DOCUMENTING PATIENT PROCEDURES

(71) Applicant: CareView Communications, Inc, Lewisville, TX (US)

(72) Inventor: Steven Gail Johnson, Highland Village, TX (US)

(73) Assignee: CareView Communications, Inc., Lewisville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/923,778

(22) Filed: Jun. 21, 2013

(65) Prior Publication Data

US 2013/0290015 A1  Oct. 31, 2013

Related U.S. Application Data

(63) Continuation of application No. 12/589,654, filed on Oct. 27, 2009, now Pat. No. 8,471,899.

(60) Provisional application No. 61/119,355, filed on Dec. 2, 2008.

(51) Int. Cl.
*G06Q 10/00* (2012.01)

(52) U.S. Cl.
USPC .................................................. 705/2; 705/3

(58) Field of Classification Search
USPC .......................................................... 705/2–3
See application file for complete search history.

(56) References Cited

U.S. PATENT DOCUMENTS

| 4,608,559 A | 8/1986 | Friedman et al. |
| RE32,327 E | 1/1987 | Biba et al. |
| 4,885,795 A | 12/1989 | Bunting et al. |
| 5,343,240 A | 8/1994 | Yu |
| 5,574,964 A | 11/1996 | Hamlin |
| 5,798,798 A | 8/1998 | Rector et al. |
| 5,995,146 A | 11/1999 | Rasmussen |
| 6,195,797 B1 | 2/2001 | Williams, Jr. |
| 6,259,443 B1 | 7/2001 | Williams, Jr. |
| 6,311,268 B1 | 10/2001 | Chu |
| 6,317,885 B1 | 11/2001 | Fries |
| 6,323,896 B1 | 11/2001 | Dahmani et al. |
| 6,323,897 B1 | 11/2001 | Kogane et al. |
| 6,429,233 B1 | 8/2002 | Oguri et al. |

(Continued)

FOREIGN PATENT DOCUMENTS

| WO | WO0018054 A2 | 3/2000 |
| WO | WO02063880 A1 | 8/2002 |

*Primary Examiner* — Tran Nguyen
*Assistant Examiner* — Rajiv Raj
(74) *Attorney, Agent, or Firm* — Faegre Baker Daniels LLP

(57) ABSTRACT

The local surveillance sub-system recognizes that a patient medical procedure has or will soon commence by sensing the presence of a healthcare professional in or near the surveillance area, and in response, creates a separate patient medical procedure A/V file for the surveillance data that will be captured. A dedicated procedure remote may be provided for receiving manual interactions from HC professionals present for a procedure or, alternatively, the local surveillance sub-system may autonomously interact with a personal security token device possessed by the HC professional. A procedure data file is also created that holds all of the pertinent information concerning the procedure that is known by the local surveillance sub-system. The patient procedure surveillance A/V file is given a higher priority than ordinary surveillance data captured by the local surveillance sub-system and is then copied to a nonvolatile memory.

20 Claims, 12 Drawing Sheets

(56) References Cited

U.S. PATENT DOCUMENTS

| | | |
|---|---|---|
| 6,456,320 B2 | 9/2002 | Kuwano et al. |
| 6,457,057 B1 | 9/2002 | Kageyu et al. |
| 6,529,233 B1 | 3/2003 | Allen |
| 6,757,909 B1 | 6/2004 | Maruo et al. |
| 6,803,945 B1 | 10/2004 | Needham |
| 6,897,781 B2 | 5/2005 | Cooper et al. |
| 7,078,676 B2 | 7/2006 | Smith et al. |
| 7,477,285 B1 | 1/2009 | Johnson |
| 8,471,899 B2 | 6/2013 | Johnson |
| 2002/0019984 A1 | 2/2002 | Rakib |
| 2002/0044059 A1 | 4/2002 | Reeder et al. |
| 2002/0069417 A1 | 6/2002 | Kliger et al. |
| 2002/0104098 A1 | 8/2002 | Zustak et al. |
| 2002/0147982 A1 | 10/2002 | Naidoo et al. |
| 2002/0163577 A1 | 11/2002 | Myers |
| 2003/0010345 A1 | 1/2003 | Koblasz et al. |
| 2003/0025599 A1 | 2/2003 | Monroe |
| 2004/0075738 A1 | 4/2004 | Burke et al. |
| 2004/0105006 A1 | 6/2004 | Lazo et al. |
| 2006/0024020 A1 | 2/2006 | Badawy |
| 2007/0136102 A1 | 6/2007 | Rodgers |
| 2009/0278934 A1 | 11/2009 | Ecker et al. |
| 2010/0134609 A1 | 6/2010 | Johnson |

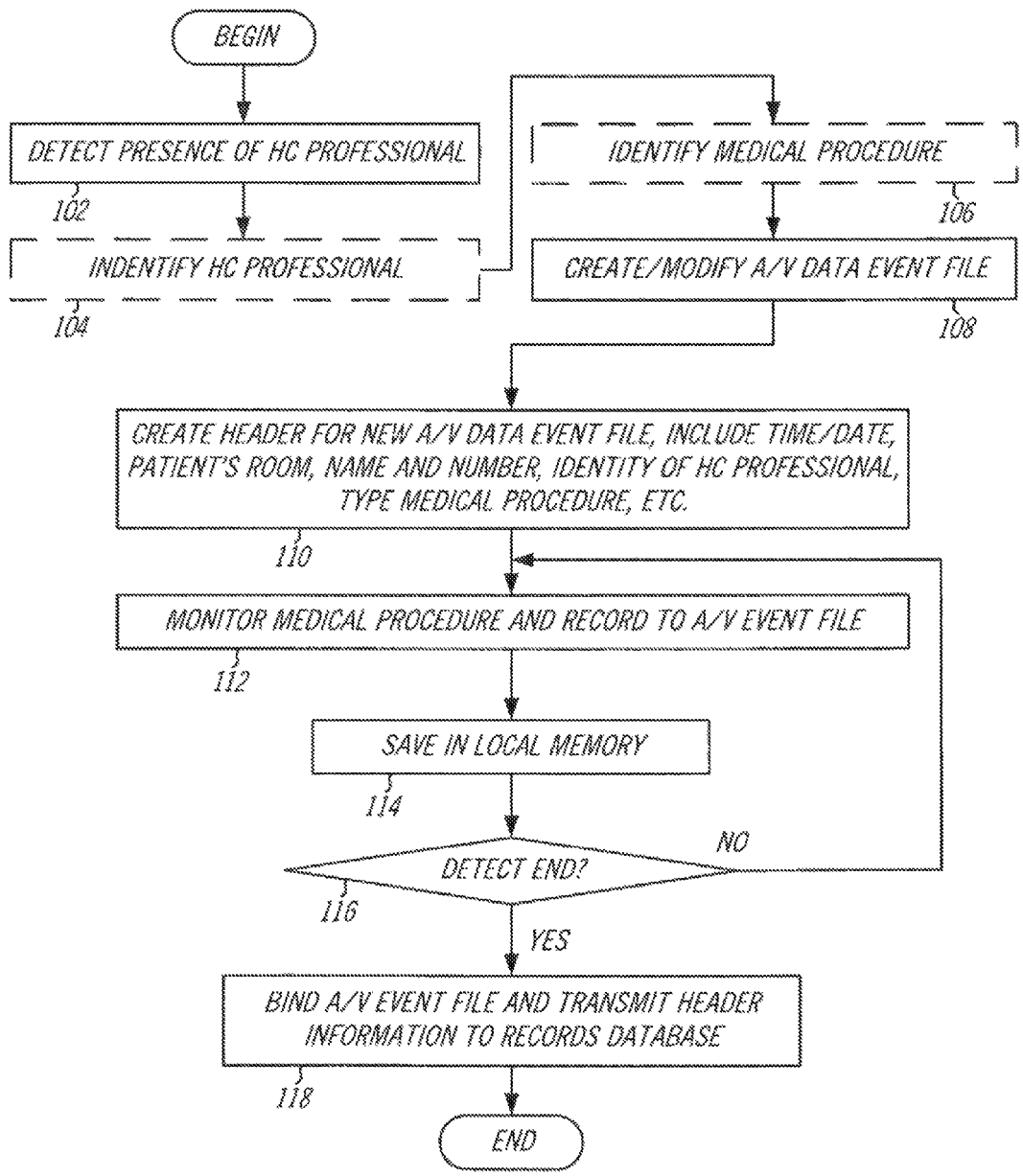

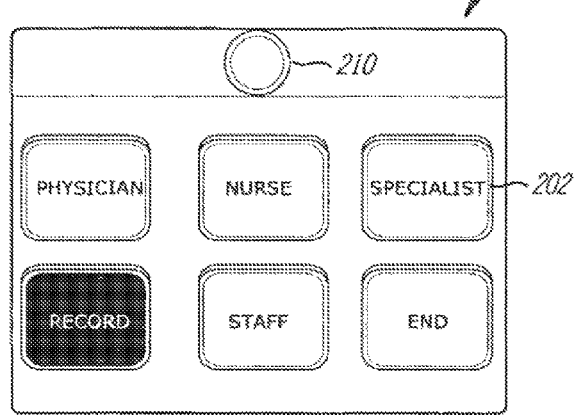
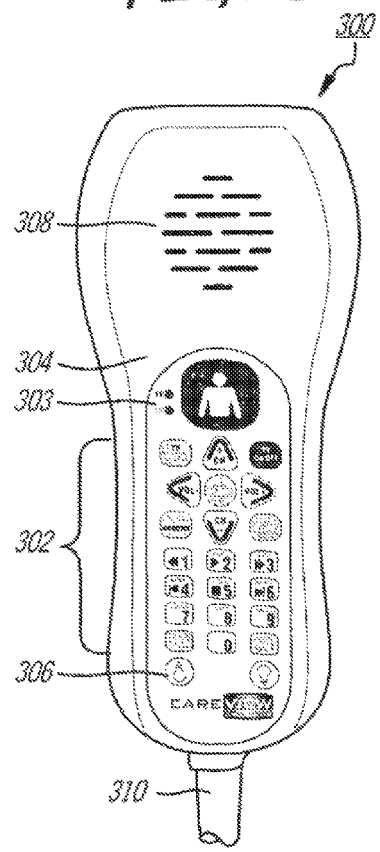
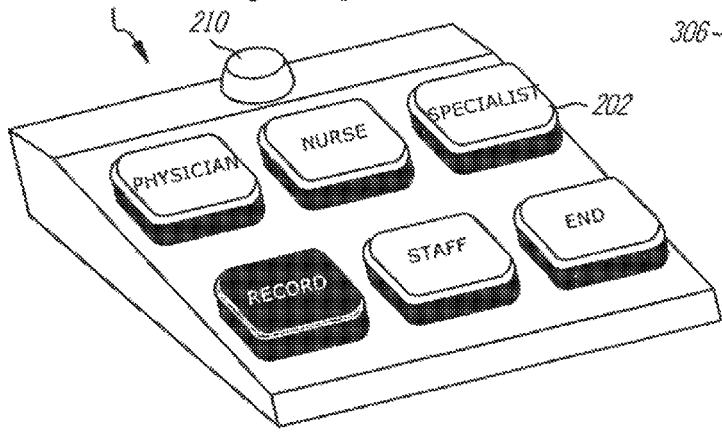

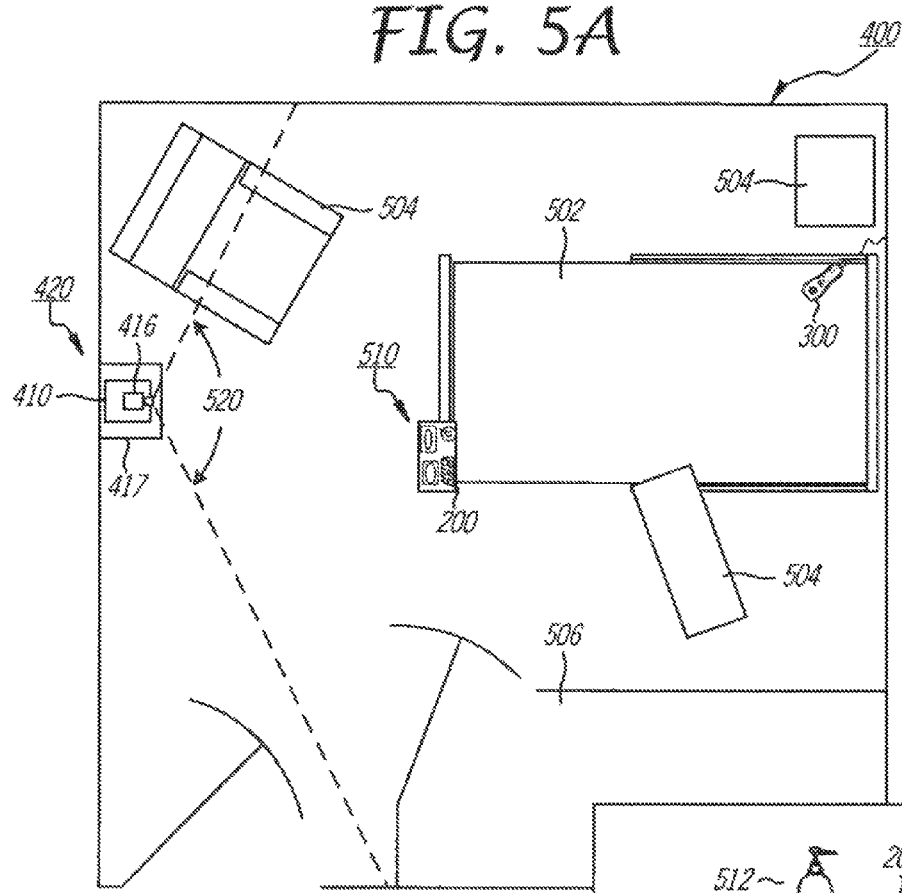
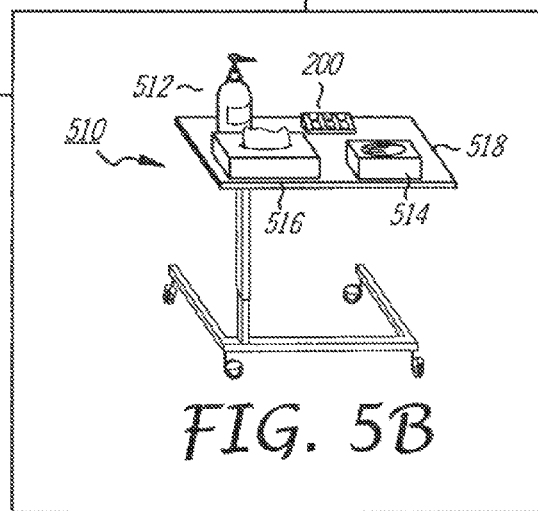

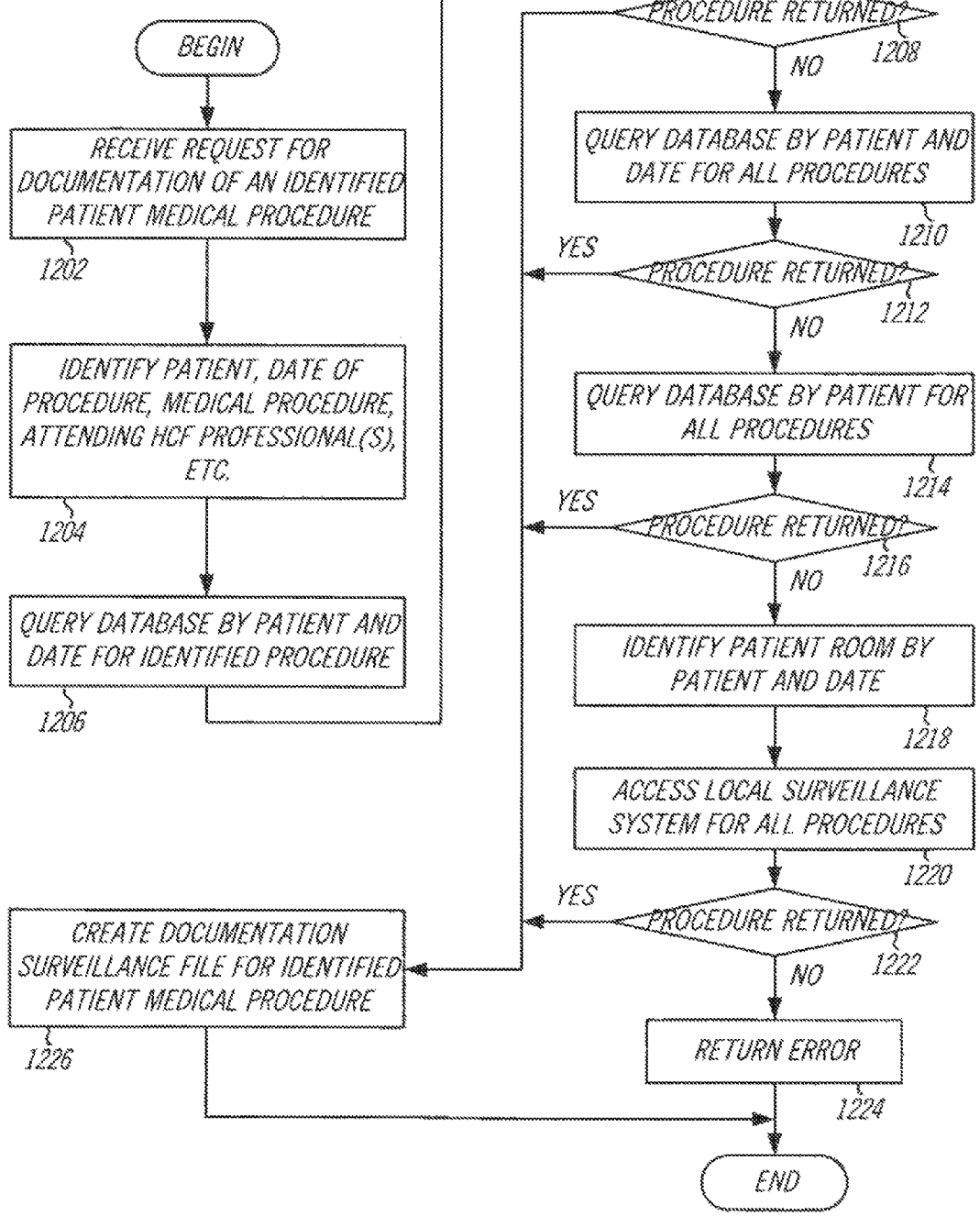

SYSTEM AND METHOD FOR DOCUMENTING PATIENT PROCEDURES

CROSS-REFERENCE TO RELATED APPLICATIONS

This application is a continuation patent application of U.S. Pat. No. 8,471,899, issuing on Jun. 25, 2013, which claims the benefit of priority of U.S. provisional patent application No. 61/119,355 filed Dec. 2, 2008, the benefit of each of which is claimed, and each of which are incorporated herein by reference in their entireties.

BACKGROUND OF THE INVENTION

The healthcare industry is a complicated, highly regulated industry that provides a product for serving every type of human condition in every combination possible. As such, detailed documentation of patient diagnosis, conditions, treatments, procedures and the frequency and time of each is mandatory.

Contrary to general belief, a hospital is not paid based on what the detailed bill indicates. Hospitals are generally paid on a Diagnostic Related Group (DRG) which is based on the patient's diagnosis that was the primary reason for admission to a hospital, complications involved with the patient's condition and/or during the patient's hospitalization and procedures performed during the hospitalization. Each different DRG (there are over 500) provides for different reimbursement. Furthermore, within a "grouping", there are different sub-categories of reimbursement that are driven by the complications and treatment of those complications.

As an example, assume a patient is admitted to a hospital for congestive heart failure (CHF) and arrived from a nursing home with decubitus ulcers (bed sores). The patient's diagnosis would be CHF with complications, decubitus ulcers. Reimbursement for CHF with no complications would be one amount, for instance $4,000.00; reimbursement for CHF with complications would be an additional amount, for instance $2,000.00 or a total of approximately $6,000.00. However, documentation must be provided to support coding that this type of ulcer did exist and was treated. Treatment for bed sores is a combination of continually moving the patient to avoid the sores getting infected and may result in a bedside debridement (removal of the ulcer at the bedside). Documentation is generally provided in the form of the nurse remembering what was done at the bedside and then memorializing the medical procedure that was performed at the bedside in the patient's medical record (paper or electronic) upon returning to the nursing station.

From the time a nurse leaves the nursing station, enters a patient's room, performs treatment, returns to the nursing station and documents the events that took place in each patients room, many opportunities for disruption and interruption can transpire. Some studies suggest that up to thirty-eight percent (38%) of healthcare provider billings do not have complete coding and supportive documentation, thereby reducing reimbursement for that particular patient's admission and causing the entire system to subsidize these shortfalls in reimbursement.

Starting in October 2008, the Center for Medicare and Medicaid Services (CMS) (the Medicare program) will no longer reimburse hospitals for errors or non-events that took place during the patients stay. Using the same example of the patient with CHF and bed sores discussed above, it will now be necessary to document that fact that the patient had this condition "before" arriving at the hospital and was not caused by the hospital. CHF is easily proven to the satisfaction of CMS (fluid in the lungs, EKG tests, enzyme testing), but it is not unusual for elderly patients to develop bed sores if they have been lying in a bed for an extended period of time in the same position. However, it is much more difficult to document conditions such as bed sores that might develop in either facility. Care must be taken to meticulously document every existing condition that might require treatment during the stay at the facility, whether or not that condition is the primary reason for the patient being admitted to the facility.

Finally, it has been reported that insurers and CMS routinely require additional support for medical procedures and charges documented on the patient's bill. Some of those procedures may even require supplemental supporting documentation to corroborate the medical procedures and charges. In addition, up to 20% of all charged items are routinely disallowed by insurers and CMS, essentially without comment or any explanation. It is then up to the healthcare facility to provide persuasive documentation in support of the medical procedures and charges. In most cases, the only support can be found in the medical records, which may have already been submitted. In the vast majority of cases, the only type of supplemental supporting documentation that can be proffered is a written description of the medical procedures by a physician or charge nurse. Documentation that is not temporal with a medical procedure is by far the least persuasive type of support that can be provided.

Aside from patient billing matters, the quality of patient care is always best when all the facts are known and documented. Physicians rely on this documentation to become knowledgeable of the patients condition, improvement or deterioration, and the frequency of events and treatments. They need 100% of the information . . . not 62% of the information. If the written patient record is incomplete or unavailable, the quality of patient care may suffer.

BRIEF SUMMARY OF THE INVENTION

The present invention is directed to a system, method and software product for documenting patient medical procedures. The present invention relates to a patient surveillance system comprising at least video and audio documentation applications that allows a healthcare facility to automatically document a medical procedure with surveillance A/V data and to direct a copy of the A/V to a nonvolatile local memory. The local surveillance sub-system constantly captures video and/or audio data from the surveillance area in, for instance, a patient room, and transmits that data to a monitoring station on the HCF distribution network. That surveillance A/V data may be used for documenting patient medical procedures, but present volumes of information that must be searched for a particular A/V sequence needed for documentation.

Initially, the present patient medical procedure documentation system senses the presence of a healthcare (HCF) professional in or near the surveillance area. The "sensing" may be autonomously via a transponder identification device in the possession of the HC professional, or may be manually invoked by the HC professional. A dedicated procedure remote may be provided for receiving manual interactions from HC professionals present for a procedure. The local surveillance sub-system recognizes that a patient medical procedure has or will soon commence and creates a separate patient medical procedure A/V file for the surveillance data that will be captured. A procedure data file is also created that holds all of the pertinent information concerning the procedure that is known by the local surveillance sub-system. That data file can be edited or amended at any time locally by the HC professional(s) present for the procedure. The patient medical procedure surveillance A/V file is prioritized higher than ordinary surveillance data captured by the local surveillance sub-system and retained in a nonvolatile memory that is separate from the primary memory of the surveillance sub-system. The local surveillance sub-system captures surveillance A/V data that is copied to the nonvolatile memory until the system senses that the procedure has ended. The end of a procedure may be signified by a command from an HC professional present or by the expiration of a predetermined time period, or by the local surveillance sub-system not detecting any movement in the surveillance area for a predetermined time period. Then, an end-of-procedure message is transmitted across the HCF distribution network. The corresponding patient medical procedure surveillance A/V file resides in a local nonvolatile until it can be downloaded to a central storage at the healthcare facility.

BRIEF DESCRIPTION OF THE SEVERAL VIEWS OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

FIG. 1 is a flowchart of a generic process for documenting a medical procedure using the patient surveillance system in accordance with one exemplary embodiment of the present invention;

FIGS. 2A and 2B are top and oblique views, respectively, of a medical procedure remote interface for initiating a medical procedure surveillance A/V data file which requires minimal interaction from a HC professional in accordance with one exemplary embodiment of the present invention;

FIG. 3 is a diagram of a pillow speaker with integrated medical procedure interface functionality for providing detailed information to present patient medical procedure documentation system for initiating a medical procedure surveillance A/V data file in accordance with one exemplary embodiment of the present invention;

FIGS. 5A and 5B are views of a patient room with the present patient medical procedure documentation system and hand cleaning/disinfectant station, respectively, in accordance with one exemplary embodiment of the present invention;

FIG. 12 is a flowchart illustrating a process for documenting patient medical procedures using surveillance A/V files corresponding to the patient medical procedure in accordance with an exemplary embodiment of the present invention.

Figure 4:
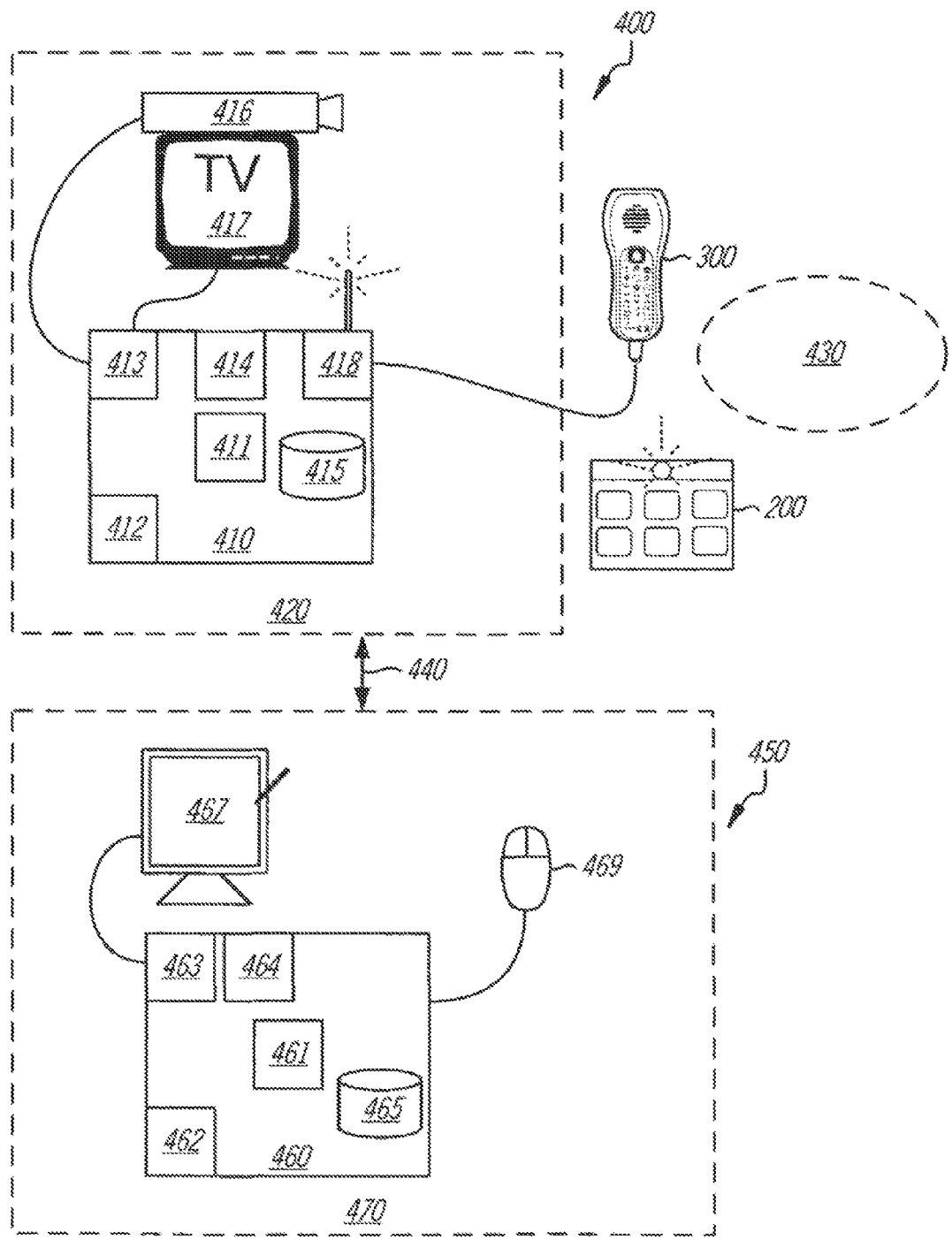
FIG. 4 is a diagram of the logical components used in the present patient medical procedure documentation system in accordance with still another exemplary embodiment of the present invention.

Other features of the present invention will be apparent from the accompanying drawings and from the following detailed description.

DETAILED DESCRIPTION OF THE INVENTION

| Element Reference Number Designations | |
|---|---|
| 200: | Procedure remote |
| 202: | Identification buttons |
| 210: | Transmitter |
| 275: | |
| 300: | Medical procedure/pillow speaker interface |
| 302: | User interface |
| 303: | Status lights |
| 304: | Nurse call button |
| 306: | Room lighting |
| 308: | Speaker |
| 310: | Transmitter/connector |
| 400: | Patient room |
| 410: | Camera control device |
| 411: | Processor unit |
| 412: | Network controller |
| 413: | Video processor |
| 414: | Primary nonvolatile memory |
| 415: | Secondary nonvolatile memory |
| 416: | Video camera |
| 417: | Video monitor |
| 418: | Receiver interrogator and medical procedure remote interface |
| 420: | Local surveillance sub-system |
| 430: | Autonomous sensing device |
| 440: | Distribution network |
| 450: | Nurse station |
| 460: | Nurse monitor device |
| 461: | Processor unit |
| 462: | Network controller |
| 463: | Video processor |
| 464: | Primary nonvolatile memory |
| 465: | Secondary nonvolatile memory |
| 466: | Video camera |
| 467: | Video monitor |
| 468: | Audible alarm |
| 469: | Manual interface device |
| 470: | Monitor sub-system |
| 502: | Bed |
| 504: | Furniture |
| 506: | Lavatory |
| 510: | Hand cleaning/disinfectant station |
| 512: | Germicidal disinfectant |
| 514: | Protective gloves |
| 516: | Wipes |
| 518: | Station table |
| 520: | View angle |
| 700: | Procedure interface |
| 710: | Computer (PC, laptop, net device) |
| 741: | Transmission medium |
| 742: | Network switch |
| 743: | Broadband connection |
| 744: | Network storage |

-continued

| | Element Reference Number Designations |
|---|---|
| 745: | Patient administration |
| 746: | Network server/router/firewall |
| 748: | Network system administration |
| 800: | Procedure remote interface |

In the following description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following description is, therefore, not to be taken in a limiting sense. For clarity of exposition, like features shown in the accompanying drawings are indicated with like reference numerals and similar features as shown in alternate embodiments in the drawings are indicated with similar reference numerals.

Accurate documentation of patient information is critical to a healthcare facility (HCF) and is a primary responsibility of anyone who comes in contact with a patient. Traditionally, these professionals include doctors, nurses, healthcare specialists and administrative professionals. As used throughout hereinafter, the term healthcare (HCF) professional will synonymously for any healthcare practitioner that may frequent an patient's room of a healthcare facility, including technicians, general facilities staff, housekeeping staff, nurse's aides, etc., in addition to those HC professionals identified directly above. Almost as importantly, that documentation should readily be available to HCF administrators. The types of patient events that necessitate documenting include patient movement, especially movements outside the prescribed bounds, the presence or absence of persons in a patient room, medical procedures, therapy, housekeeping, counseling and consultations. Typically, documentation is in the form of written or audio records that are transcribed into the patient's records.

Recently however, HCFs have begun placing video surveillance equipment in patient areas such as examination rooms, therapy rooms and patient rooms, corridors and even lavatories. Conventionally, during operation this equipment generates huge volumes of surveillance A/V data that must be transmitted over existing networks to a remote monitoring station and, if necessary, to dedicated storage servers. The bandwidth of most HCF distribution networks is usually insufficient for carrying both the normal data traffic for the healthcare facility and surveillance A/V data. Hence, even though a patient surveillance device may be in the patient's room, it cannot necessarily be relied on due to network bandwidth constraints. This shortcoming has been addressed in U.S. patent application Ser. No. 10/735,307 to Johnson entitled Non-Intrusive Data Transmission Network for Use in an Enterprise Facility. There, the primary surveillance data transmission medium is an existing coaxial CATV network. Hence, the coaxial CATV network carries surveillance data as well as CATV programming. A set-top control device and surveillance camera control device replaces, or is integrated in the traditional CATV set-top box in the patient rooms. The set-top control device arbitrates with the coaxial network for transmitting A/V data captured in the individual patient rooms. Even using the coaxial network for surveillance traffic does not guarantee that the network is up and available for A/V traffic, or has the bandwidth capacity to carry all of the surveillance data collected from each patient room. Therefore, the set-top control device is configured with a video processor and a local memory for varying the transmission rates on the coaxial network and, if necessary, for storing the surveillance data locally for retrieval in the future. These improvements greatly increase the available network bandwidth to accommodate more surveillance data and the likelihood that the data are available even after the coaxial network goes down.

Aside from the problem of available network bandwidth, another shortcoming of prior art patient surveillance systems is that they cannot distinguish between pertinent surveillance data and surveillance data that is less important. Some type of surveillance data may have more significance than others, but without some mechanism for discriminating data, all surveillance data is equally important to the surveillance system. U.S. patent application Ser. No. 12/151,452 filed May 6, 2008, entitled System and Method for Predicting Patient Falls describes a set-top control device that contains intelligence that enables the video processor to discriminate video data that is of low importance, such as sequential video frames without motions. The surveillance system is further improved by implementing a patient fall prediction system in the set-top control devices of HCF's existing surveillance monitoring system. The prediction system not only more accurately discriminates important surveillance A/V data from data of lesser importance for efficiently allocating storage space and transmission bandwidth, it also provides a means for triggering an alarm when the patient traverses high risk areas, such as the edges of a bed or chair, the side of a tub, a shower entry, or even an entryway threshold. While each of these inventions solve a particular problem facing the healthcare industry, the dilemma of accurately documenting patient event data in a manner that it is easily accessed by an HCF administrator has not yet been addressed.

The present invention provides a mechanism that is seamlessly incorporated into an HCF's surveillance system for identifying important patient events, documenting them with surveillance A/V data and saving the surveillance A/V files to a local storage, along with the corresponding identification data, for future retrieval. Moreover, as will be discussed below, in many embodiments the present patient medical procedure documentation system operates autonomously, without manual intervention. This is highly desirable as it provides an additional measure of documentation over the written patient records prepared by the healthcare provider, with little or no input from the HC professionals that are present during the procedure.

Essentially, the present patient medical procedure documentation system recognizes that a HC professional (or a HCF procedure provider) is present in a surveillance area and creates a separate data file for all surveillance A/V data collected while the HC professional is present. At a threshold level, the present patient medical procedure documentation system senses the presence of a HC professional and begins a medical procedure A/V data file associated with the professional. The mere fact that a stream of surveillance data can be distinguished from all other data by the presence of the HC professional greatly reduces the workload of ferreting through endless streams of A/V data for documentation of a medical procedure.

Optimally, the present patient medical procedure documentation system identifies the HC professional by her job title/description/position, name or employee number and writes that information to an A/V file. This information further simplifies the task of identifying a particular A/V data stream associated with a particular procedure because in most cases the identity of the HC professional for the procedure is known, consequently the A/V record need only be searched for data where the particular HC professional is present. Here, it should be mentioned, that although the captured surveillance data is expected to be in the form of audio and video media, it may instead be one or the other. Still further, the present patient medical procedure documentation system may provide a mechanism for the HC professional, or some other person, to bind an A/V data file with all data that is pertinent to the medical procedure. For instance, a separate interface device for entering additional data that might be used to, for instance, search fields or keyword identifiers for sorting A/V data files. The types of data vary. For instance, the type of procedure, its billing code, the identity of the HC professional present and employee number, the identities of HCF personnel present (in addition to the HC professional who performed the patient procedure), comments by the HC professional made before, during or after the procedure and even a separate audio tract by the HC professional to be transcribed into the medical record (as opposed to, or in addition to, the current practice of the HC professional creating a separate audio tape from the written patient record that is later transcribed into a formal medical record).

Furthermore, in accordance with some aspects of the present invention, the present patient medical procedure documentation system will write the data collected from the surveillance area to a file of streaming A/V data, or in accordance with other aspects of the present invention, the data collected from the surveillance area may be appended to each image frame, audio packet or other convenient subdivision of the A/V data stream.

In any case, the present patient medical procedure documentation system supplements more permanent data relating to the surveillance area with more transient information that is indicative of an important patient event, such as a medical procedure. For instance, a patient monitoring device may be permanently disposed in the patient rooms of an HCF. All A/V data captured in the respective patient rooms is labeled with location information, such as a room number or area designation and a timestamp. Hence, any surveillance data saved by the system may be retrieved by the location of the surveillance camera and time. While this provides a minimal filter for discriminating surveillance data, the amount of time necessary for a HCF administrator to ferret out A/V documentation for a particular procedure may be quite extensive. In accordance with one exemplary embodiment of the present invention, the present invention further binds the A/V data with information relating to the status of the HC professional present in the surveillance area. Ideally, that information identifies the HC professional's job title or description or her position with the HCF. Detecting the presence of an identifiable HC professional in an A/V data stream greatly reduces the amount of time that is necessary for finding A/V documentation for a particular medical procedure. Most procedures require the presence of an HC professional with a particular skill set. For instance, if an administrator needs documentation that a particular patient received preventative care for bedsores, the administrator merely selects the surveillance A/V files from the patient's room when an aide, nurse or physician was present. Alternatively, if the administrator needs to know the time and frequency of a patient having his blood pressure checked, the administrator may instead access all surveillance A/V files from the patient's room in which a nurse or physician was present, more likely a nurse. Documentation for more complicated medical procedures that require the presence of a physician are easily retrieved from the A/V record by filtering files in which a physician was present. Obviously, without labeling A/V surveillance files with the procedure identification, it may be necessary for the administrator to review several data files for one documenting the target procedure, however, the amount of data to be reviewed is reduced from hours to, perhaps, a very few minutes when an HC professional qualified to administer the procedure is present.

In accordance with still another exemplary embodiment of the present invention, each time the present patient medical procedure documentation system senses the presence of an HCF in or near the surveillance area, it automatically saves the A/V data stream to a local, nonvolatile memory and flags it as a protected file. As such, that data is given a higher priority from overwriting. This procedure has two features that protect potentially important surveillance A/V data from deletion. First it removes the data from the control of the network transmission arbiter and second, it ensures that at least one documentation copy of the procedure is warehoused, at least semi-permanently. Conventional network surveillance systems attempt to transmit all captured surveillance A/V data to a central retention server in real-time. Often there is no contingency other than overwriting the data if the network or server cannot accept the data in near real-time.

More particularly, the patient surveillance system of the present patient medical procedure documentation system generally comprises two separate nonvolatile memories. The first is a smaller capacity memory for temporarily storing video data frames (and the associated audio) prior to network transmission, between video processing stages and during, such as a solid state flash memory. The second memory is also a non-volatile memory but has a much larger capacity. The primary reason for bifurcating the memory is cost. While the entire memory may be constructed of a non-volatile solid state memory, it is simply too expensive of a medium for storing the amount of A/V surveillance data that must reside locally. For this reason the second memory is usually a hard drive. In either case, the A/V surveillance data residing in the second memory is available for downloading locally via the patient surveillance system or remotely over the network.

Still more particularly, the patient surveillance system of the present patient medical procedure documentation system comprises data and video processing capacity for detecting, sensing or identifying video sequences associated with a medical procedure and then to bind those A/V data sequences with information that is pertinent to the procedure. That information is usually obtained simultaneously with detecting or sensing. In accordance with one exemplary embodiment of the present invention, the patient surveillance system senses the presence of a HC professional in or near the surveillance area. The patient surveillance system may comprise a transceiver or interrogator for sensing the presence of a particular type of security token, i.e., a small hardware device with built-in authentication mechanisms unique to the possessor of the device. In that case, the HC professional carries a compatible security token device, such as transponder key FOB, RFID asset management, Bluetooth or the like. In sensing the presence of the HC professional, the patient surveillance system interrogates the security token for information about the holder, such as the identity of its owner, employee number, position, status, authority and security level, etc. It should be mentioned that the security token may actively transmit security information and/or negotiate with the transceiver/interrogator or may instead be a passive device that is interrogated by the transceiver/interrogator or, alternatively, be a completely passive device that generates security keys that must be manually entered to the patient surveillance system by a HCF processional that is present for the procedure.

The patient surveillance system is constantly monitoring the surveillance area in a patient's room by video and perhaps audio capture devices. As might be appreciated, this type of surveillance creates an inordinate amount of data associated with any single patient's stay in a healthcare facility. Multiply that amount of surveillance data by the number of patient rooms, examination rooms, emergency stations and medical procedure rooms and it becomes evident that maintaining the surveillance data requires the instantiation of a new department solely for handling the electronic surveillance data. Furthermore, it is doubtful that any facility's IT, except possibly the smallest healthcare facility, could provide the network bandwidth that is necessary to support transmission of the surveillance data to a central data storage. Even assuming these problems could be overcome, searching the global mass of surveillance data for documentation of a single (or group) of medical procedures for a patient would require hours of viewing time by a qualified professional for identifying the surveillance record for a particular patient and then viewing the patient's surveillance record for evidence of a particular medical procedure.

The present invention overcomes the shortcomings discussed above by identifying surveillance data for a patient as tentatively being medical procedure documentation and then taking extraordinary measures for protecting the medical procedure documentation.

FIG. 1 is a flowchart of a generic process for documenting a medical procedure using the patient surveillance system depicted in FIG. 4, which incorporates several input devices for the delineating the medical procedure documentation from other surveillance data captured by a patient surveillance system. FIGS. 2A, 2B and 3 depict exemplary interface devices for identifying surveillance data as being associated with a medical procedure and for entering information pertinent to the procedure to the surveillance data.

Before discussing the devices and methodology of the present invention, it should be mentioned that the healthcare professionals, like anyone else, are more likely to embrace a new technology or procedure that entails little or no learning and requires little or no extra effort in using. Hence, the present patient medical procedure documentation system may be implemented as a completely passive system in which the patient medical procedure documentation system makes all decisions regarding the identification of medical procedure surveillance data. Alternatively, the present patient medical procedure documentation system may be implemented as a more active system in which the healthcare professional must interact with the system for inputting certain data regarding the identification of medical procedure surveillance data and/or the identity of the HC professional(s) present or other data pertinent to the procedure. In general, however, the present patient medical procedure documentation system may require some type of human interaction for providing pertinent information that identifies the type of medical procedure and/or the HC professional(s) present during the medical procedure. However, much of this interaction may be accomplished beforehand by inputting the data to the system at a remote location. The inputted data is then stored at the local patient surveillance system in the patient's room, or the like, until the procedure is performed. Still another alternative is for the HC professional to initiate the creation of a medical procedure surveillance file and manually enter the necessary data pertaining to the procedure. These and other features of the present invention will become clear with the description of the figures.

Turning to FIG. 1, a flowchart is illustrated that shows a generic process for providing documentation of a medical procedure in accordance with an exemplary embodiment of the present invention. The process is executed within the patient medical procedure documentation system and more particularly the entire process may be executed within a local camera control device of the system, such as that depicted in FIG. 4. The local camera control device may be embodied as part of a set-top box as described in copending U.S. patent application Ser. Nos. 10/735,307 and 12/151,452, or instead may be embodied in a dedicated patient surveillance system, or the like. In either case, one function of the system is to identify portions of the surveillance video (or audio) stream for a medical procedure and to protect that data as a local A/V data file that can be accessed anytime thereafter. As a threshold matter, most HCF's would prefer that any ambiguous A/V be treated as medical procedure data, protected and saved locally for manual (visual or audio) inspection. In that way, the HCF can be guaranteed that all medical procedure documentation is retained, while simultaneously reducing the amount of A/V data that must be manually inspected.

The process begins by the patient medical procedure documentation system detecting the presence of an HC professional (step 102). The system may sense the presence of an HC professional through a personal identification device, for instance by autonomously interrogating a security token device, transponder key FOB, an RFID asset management device, a Bluetooth device or the like that is carried on the HCF personnel. Alternatively, the system may sense the presence of an HC professional through manual interaction of a specialized medical procedure interface device. In either case, the system is alerted of the presence of a HC professional in or near the surveillance area that might indicate that a patient medical procedure is to commence. Optionally, the process identifies the HC professional by name, position, status and/or by ID, employee or badge number (step 104). As may be appreciated, at times more than one HC professional will be present. In the autonomous mode, optimally the present patient medical procedure documentation system will create a hierarchy of HC professionals that are present and associate those professionals to all possible patient medical procedures that are authorized by the group. If no other information related to the medical procedure can be ascertained by the system, the A/V data file will at least provide enough information to narrow a search to a certain medical procedures, thereby greatly reducing the amount of A/V surveillance data that must be inspected manually.

Optimally, the type of medical procedure to be performed can be identified by the system (step 106). That information may be entered manually by the attending HC professional or selected from a list of procedures that are authorized by the highest ranking attending HC professional. Alternately, the identity of the procedure may be inferred from the rank or status of the attending HC professional. Hence, by accurately detecting the presence of an identified HC professional, the present patient medical procedure documentation system can autonomously determine which types of medical procedures, if any, that the HC professional is authorized to perform. For example, upon detecting the presence of only a nurse's aide, the present patient medical procedure documentation system will correlate the status of a nurse's aide to the medical procedures authorized to be performed by the aide. Alternatively, if the highest ranking HC professional detected by the system is a nurse with RN status, then the present patient medical procedure documentation system will correlate the status of a registered nurse to the medical procedures authorized to be performed by an RN. The aim here is to eliminate all medical procedures that are not authorized to be performed by the HC professional present with the highest rank.

With at least information inferring the presence of HC professionals, the present patient medical procedure documentation system creates an A/V data medical procedure file for the upcoming stream of A/V data (step 108). A file header is created for the new patient medical procedure and all pertinent information concerning the procedure is included (step 110). From this point forward, all A/V data captured by the present patient medical procedure documentation system is treated as proprietary in the local memory over many other types of A/V data files stored to the system. This is important because the local camera control device comprises a finite amount of storage capacity. A/V data stored onto that system should be prioritized for efficient storage of A/V data. The aim is to retain high priority A/V data for future access, while overwriting lower priority data with more temporal A/V data and/or higher priority A/V data. A hierarchy of file types may be created for prioritizing the A/V data files. For instance, surveillance A/V data may be assigned the lowest priority, but surveillance A/V data in which motion is detected might be given a higher priority (see for instance copending U.S. patent application Ser. Nos. 10/735,307 and 12/151,452). A/V data files for documenting a patient medical procedure may be given an even higher priority. Hence, as memory space is needed for new surveillance A/V data, the present patient medical procedure documentation system compares the priority of the newly captured A/V data with that in the local memory for allocating storage space. Moreover, the file hierarchy may extend to prioritizing types of medical procedures, for instance, a patient rotation to prevent bedsores may have a lower priority than an EKG or another medical procedure that can only be performed by a physician or medical specialist. In any case, the present patient medical procedure documentation system is flexible enough to enable the attending HC professional to modify the information in the medical procedure surveillance A/V file header at anytime until the A/V medical procedure data file is bound.

Once a medical procedure A/V data file has been created, the present patient medical procedure documentation system monitors the procedure and captures audio and/or video to the A/V data file (step 112). Each captured video frame is immediately copied to a secondary local memory in the camera control device (step 114). An exemplary embodiment of the local camera control device will be discussed below with regard to the device illustrated in FIG. 4 below. However optimally, the secondary memory is a nonvolatile memory that accommodates moderate transfer speeds, such as a flash memory or an optical hard drive, with the capacity for storing several hours of A/V data. The aim is to provide memory space for temporarily storing medical procedure A/V data files and the associated header data. The storage architecture should provide the medical records personnel with the means for accessing the secondary memory and identifying specific medical procedure A/V data files stored thereon. As may be appreciated, other types of memory may also be used, such as an optical drive for writing to CD or DVD media, but accessing the data files thereon may be more manually intensive.

In any case, the present patient medical procedure documentation system continues writing A/V data to the open medical procedure A/V data file until the system detects an end to the medical procedure (step 116). The present patient medical procedure documentation system invokes a procedure end detection sub-process that continually tests for an end to the procedure. The procedure end detection sub-process may take one of many forms, such as by receiving a manual command from the HC professional to terminate the medical procedure A/V data file, or by detecting the end of a predetermined time period, or by failing to detect any motion in the surveillance area for a predetermined time period, or any combination of the sub-processes described above. Once the present patient medical procedure documentation system detects that the medical procedure has ended, it binds the medical procedure A/V data file with the header information and transmits the header information over a network to a medical records database for permanent storage (step 118). A data file containing some or all of the patent procedure data may then be transmitted across the HCF distribution network. Receiving an end-of-procedure message, or in fact any header information concerning a patient medical procedure, indicates that the set-top box in the patient's room may contain a medical procedure surveillance A/V data file related to the procedure file, and hence should be promptly downloaded before it can be overwritten with more temporal surveillance A/V data. Typically, the medical records database is under the control of the system administrator, but is usually accessible by the HCF medical records and patient billing departments. Once the header information is received by the system administrator, the administrator can schedule a time for downloading the medical procedure documentation, usually during off-peak hours.

As discussed immediately above, one novel feature of the present patient medical procedure documentation system is the ability to sense the presence of an HC professional that may indicate the commencement of a medical procedure. In so doing, the present patient medical procedure documentation system immediately creates a medical procedure A/V data file using audio and/or video that is captured by a patient surveillance system. The medical procedure A/V data file created by the patient surveillance system is securely saved to a local nonvolatile storage until it can be downloaded over the HCF network to a central medical records database. As also discussed, these sensing devices may be bifurcated into manual and autonomous sensing device categories. Of the two categories, the autonomous sensing devices are preferred as they require little or no manual interaction by the HC professional present during the patient medical procedure and, therefore, present less opportunity for the omission of documenting a patient medical procedure. The autonomous sensing devices usually require that HCF personnel possess a personal identification device, such as a transponder key FOB, an RFID asset management device, a Bluetooth device or the like, that can be interrogated for the owner of the personal identification device by the present patient medical procedure documentation system in cooperation with the patient surveillance system. Ultimately, an optimal sensing device is a facial recognition routine embodied on the patient surveillance system that autonomously recognizes HC professionals that are present in the patient surveillance area of the patient's room (i.e., a facial biometrics recognizer).

Manual sensing devices, on the other hand, may include legacy manual input devices such as keyboards, mice, trackballs, pointers, etc, (optimally utilizing wireless transmission technology such as RF, Bluetooth or IR). The use of these legacy manual input devices require significant interaction by the HC professional through one or more video display screens for creating a medical procedure A/V data file and/or merely identifying herself as being present in the patient surveillance area (resulting in the present patient medical procedure documentation system automatically creating a medical procedure surveillance A/V data file). Hence, these types of devices are particularly problematic in a bustling HCF environment, especially for higher level HC professionals such as physicians, medical specialist and the like. Therefore, in accordance with still another exemplary embodiment of the present invention, a medical procedure remote interface is provided which require minimal interaction for the HC professional, while providing enough information to the present patient medical procedure documentation system for the instantiation of a medical procedure A/V data file.

FIGS. 2A and 2B are top and oblique views, respectively, of a medical procedure remote interface for initiating a medical procedure A/V data file which requires minimal interaction from a HC professional in accordance with one exemplary embodiment of the present invention. Procedure remote interface 200 is essentially a remote interface device that is linked to the present patient medical procedure documentation system for detecting the presence of a HC professional who is in or near the patient surveillance area. Although the present medical procedure remote interface may be implemented in numerous configurations, the basic requirements of the device are to identify some type of information that may indicate the commencement of a patient medical procedure and to communicate that information to the present patient medical procedure documentation system.

Exemplary medical procedure remote interface 200 utilizes several manually interactive buttons which are separately labeled with some information relating to a patient medical procedure. In the exemplary device, buttons 202 are labeled "PHYSICIAN," "NURSE," SPECIALIST" and "STAFF" for identifying HC professionals that are in the surveillance area and separate "RECORD" and "END" buttons for creating and terminating a medical procedure surveillance A/V data file. Hence, if PHYSICIAN button is depressed, medical procedure remote interface 200 communicates that information to the present patient medical procedure documentation system. In turn, a medical procedure A/V data file is created which identifies a physician as being present in the patient's room.

Interface buttons 202 may be tactile or disposed on a touch screen, or alternately the manual interface of medical procedure remote interface 200 may be any highly simplified interface device such a single human interface that detects some predefined interaction by a HC professional such as a manual (or virtual) actuator, switch, lever, knob, etc., or a biometric sensor such as a voice recognizer, fingerprint reader, whole hand scanner, iris/retina recognizer, as well as a facial biometrics recognizer used in conjunction with medical procedure remote interface 200.

Also shown on medical procedure remote interface 200 is transmitter 210 for communicating with the base station portion of the patient surveillance system (i.e., a camera control device or the like). It should be appreciated that transmitter 210 is internal or barely visible on medical procedure remote interface 200. In practice, transmitter 210 may actually be a transceiver for bidirectional communication with the patient surveillance system. Transmitter 210 may operate in any wireless protocol, for instance RF, IR, Bluetooth, or even WIFI or WIFI Protected Access (WPA), legacy IEEE 802.11 or one of the evolving wireless design standards, i.e., IEEE 802.11x.

One shortcoming of medical procedure remote interface 200 discussed above is that it provides little information concerning the patient medical procedure. While this information is sufficient to create and protect a medical procedure A/V data file on a local memory, it lacks the specificity necessary that is required for a HCF billing professional to query the HCF medical records database for a specific medical procedure for a specific patient. Therefore, in accordance with still another exemplary embodiment of the present invention, a pillow speaker with an integrated medical procedure interface is disclosed. FIG. 3 is a diagram of a pillow speaker with an integrated medical procedure interface functionality for providing detailed information to present patient medical procedure documentation system for initiating a medical procedure A/V data file. Pillow speakers are well known in the prior art as being an A/V device tethered to both the patient's television and the nurse station. Conventional pillow speakers comprise a handheld unit with a speaker and usually some rudimentary television controls, e.g., channel changer, speaker volume control and an ON/OFF switch. Some more advanced prior art pillow speakers include a channel selector and often a nurse call button. By contrast, the present medical procedure/pillow speaker interface 300 comprises user interface 302 with a multiplicity of buttons for selecting CATV television channels, adjusting the volume of speaker 308, and for entering copious amounts of information to the present patient medical procedure documentation system. Typically, medical procedure/pillow speaker interface 300 is wired to the HCF's CATV and surveillance networks by wired tether 310 (this is primarily due to the high power consumption of speaker 308 and, therefore, can be eliminated in favor of a wireless connection if the speaker function is eliminated). As the presently described patient surveillance and patient medical procedure documentation systems may piggyback or parallel the HCF's CATV network, user interface 302 also provides dedicated buttons for switching to and from the CATV network to the patient surveillance system and/or the patient medical procedure documentation system. Status lights 303 are provided for identifying the current system being accessed, e.g., the CATV network or the patient surveillance network. Additionally, exemplary user interface 302 provides a telephone interface for entering textual or numeric data or a combination of the two. Also provided is room lighting control 306 and nurse call button 304 for alerting the nurse's station. The functionality of medical procedure/pillow speaker interface 300 and other types of medical procedure interfaces will become more apparent with the descriptions of FIGS. 4, 8 and 12 and the process described in the flowchart depicted in FIG. 11.

Figure 7:
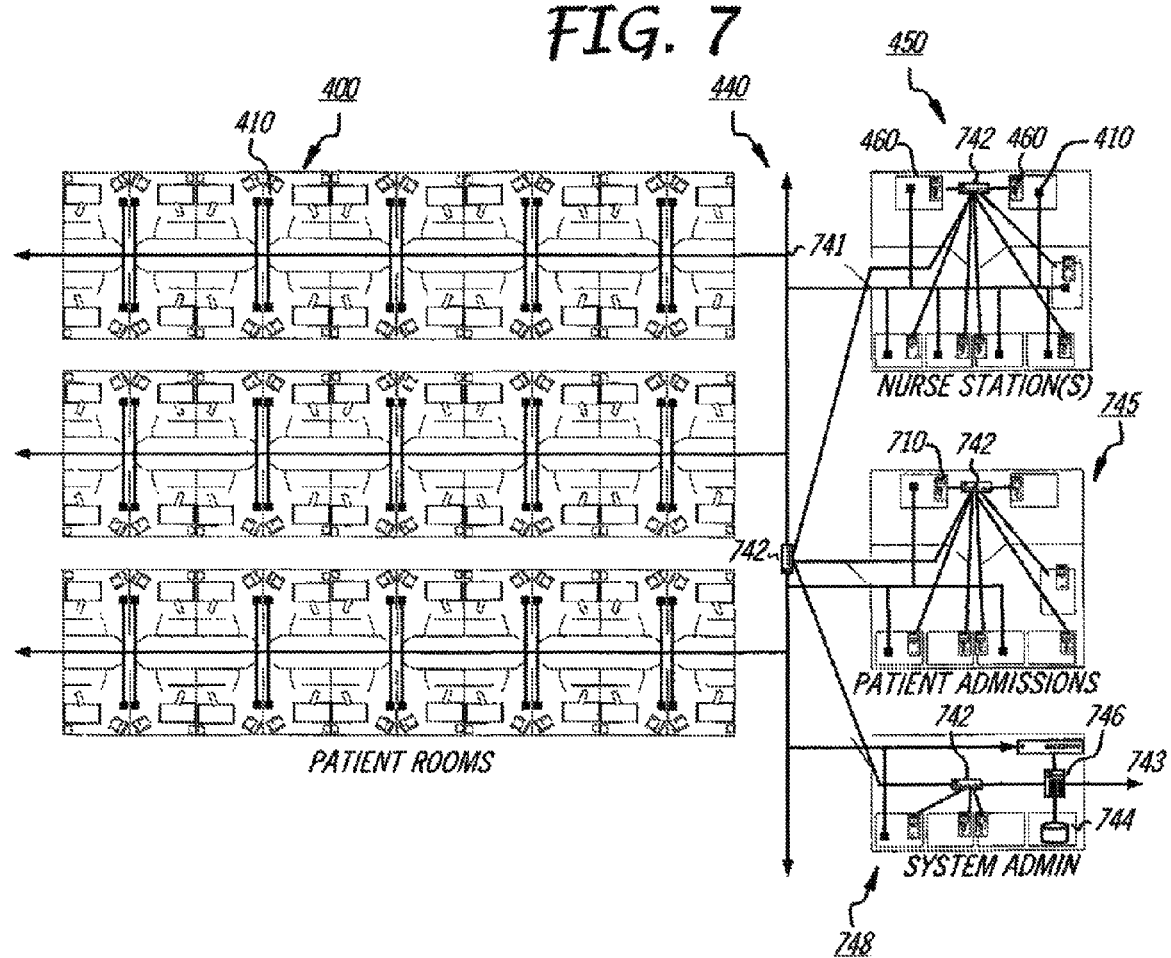
FIG. 7 is a diagram of an exemplary healthcare facility in which the present patient medical procedure documentation system may be implemented.

FIG. 4 is a diagram of the logical components used in the present patient medical procedure documentation system in accordance with still another exemplary embodiment of the present invention. Typically, the present patient medical procedure documentation system is implemented in a patient surveillance network, which usually comprises at least patient surveillance sub-system 420 and patient monitoring sub-system 470. As may be appreciated, the present patient medical procedure documentation system may also be implemented across several physical locations, such as patient room 400 (containing patient surveillance sub-system 420) and nurse station 450 (containing patient monitoring sub-system 470). The separate sub-systems may also be realized in virtually any location in the healthcare facility, such as the offices for patient administration, billing, medical records and network administration, depending on the duties of the particular location. FIG. 7 is a diagram of an exemplary healthcare facility in which the present patient medical procedure documentation system may be implemented.

The components that are typically located in patient surveillance sub-system 420, such as patient room 400, include camera control device 410 that is usually juxtaposed to television 417, but is not essential to the practice of the present invention (see FIG. 5). In most patient rooms, television 417 is installed at a central location which is also a highly advantageous viewpoint location for installing surveillance camera 416. Additionally, a microphone (not shown) may be disposed on surveillance camera 416, camera control device 410 or connected as a separate peripheral for capturing audio in the surveillance area. Hence, for many installations, camera control device 410, television 417 and surveillance camera 416 are loosely coupled together as a unit (see again FIG. 7). In any case, camera control device 410 provides the local processing, storage and network connections for the surveillance peripherals and for the present patient medical procedure documentation system. Here it should be mentioned that much of the functionality of the present invention may be embodied in a standard personal computer, however, other aspects of the present invention may require supplemental video processing and/or storage capacity. Furthermore, as may be appreciated from the description of the set-top box in copending U.S. patent application Ser. Nos. 10/735,307 and 12/151,452, camera control device 410 may also have CATV, Internet, PSTN and other capabilities that are not traditionally found in a standard personal computer.

With further regard to camera control device 410, processor unit 411 diagrammatically represents all the processing capacity, RAM and ROM memory, busses and the physical framework for storing and executing instructions for operating the other components of the control unit. Network controller 412 provides a connection to HCF distribution network 440 and to other devices connected to the HCF network, such as nurse monitor device 460 of patient monitoring sub-system 470. Video processor 413 comprises any video processing capabilities) necessary for capturing, processing and/or displaying any video and/or patient medical procedure documentation screens. Video processor 413 may be integrated in a general purpose processing system or supplement the video processing capabilities of the general purpose processing system. As such, video processor 413 is responsible for receiving the captured video frames from video camera 416, analyzing video for motion (see copending U.S. patent application Ser. Nos. 10/735,307 and 12/151,452), prioritizing video frames based on content or external factors (such as labeling the frames as documentation for a patient medical procedure) and compiling medical procedure information screens for display on the local monitor, such as TV 417 (see FIG. 10).

Camera control device 410 also comprises receiver/interrogator and medical procedure remote interface 418 for communicating with a medical procedure sensing device (a manual or autonomous remote interface for sensing an event indicative of the commencement of a patient medical procedure). Optimally, receiver/interrogator and medical procedure remote interface 418 provides multiple communications ports for connecting with multiple types of medical procedure sensing devices, e.g., autonomous sensing devices 430, medical procedure remote interface 200, medical procedure/pillow speaker interface 300 and/or some type of legacy interface device. As discussed elsewhere above, the medical procedure remote device may operate autonomously (usually by sensing the presence of an HC professional through autonomous sensing devices 430) or manually by receiving manually invoked communication from a HC professional. In either case, the aim is for camera control device 410 to receive supplemental information indicative of the commencement (and possibly termination) of a patient medical procedure. The receipt of this information enables camera control device 410 to flag any subsequently captured A/V data as documentation for the information indicative of a patient medical procedure. Hence, that A/V data may be prioritized and/or backed up locally for access in the future. To that end, camera control device 410 comprises at least one nonvolatile memory for storing A/V data documentation of a patient medical procedure.

As depicted in FIG. 4, camera control device 410 further comprises primary nonvolatile memory 414 and secondary nonvolatile memory 415, for storing different classes of captured A/V data. The storing operations of camera control device 410 will be discussed below with regard to FIGS. 8 and 9, however it should be appreciated that surveillance data received by camera control device 410 may comprise varying degrees of importance. Most surveillance data received by camera control device 410 is of relatively low importance. That surveillance data are simply transmitted to monitoring device 460, in near real time, for temporal monitoring by an HC professional, such as a nurse at nurse station 450. Since that data has a relatively low priority, it will be the first data to be temporally overwritten by fresher surveillance data received at camera control device 410. More important surveillance data received by camera control device 410 may be flagged for further review by an HC professional. This type of data might include A/V data that failed to be immediately transmitted over distribution network 440 due to network bandwidth or operation issues. Various techniques may be applied to this data for achieving a rapid resolution to the problem, such as alarms, frame rate reduction and locally backing up the A/V data.

Another class of data that should be treated separately is surveillance data relating to patient medical procedures. This type of surveillance data is associated with information received by receiver/interrogator and medical procedure remote interface 418 that is indicative of a patient medical procedure. All surveillance data captured within a time window of the receipt of patient medical procedure information may be treated as documentary evidence of that patient medical procedure. Hence, surveillance data retained in primary nonvolatile memory 414 prior to receiving the patient medical procedure information may be considered as documentation of a patient medical procedure.

Before proceeding, it should be mentioned that surveillance A/V data may be retained in one of several formats. One retention format involves storing the sequentially captured images frames as separate image frame files. Patient procedure information received at patient surveillance sub-system 420 is included in the frame header for corresponding image frames. This retention format is more useful for streaming video across the HCF distribution network; if documentation of a patient medical procedure is needed, each of the image frames must be searched and returned separately and then combined into a single documentation surveillance A/V file. A second retention format involves storing all of the captured image frames for a particular patient medical procedure as a single surveillance A/V file. The surveillance A/V file is created upon receiving information indicating that a new patient medical procedure is commencing. Video image frames currently in primary nonvolatile memory 414 that were captured within a predetermined time window are included in the newly created procedure surveillance A/V file. All A/V data captured at patient surveillance sub-system 420 are bound to the procedure surveillance A/V file until an end-of-procedure event is logged. The end-of-procedure event may be any information indicative of an end of the patient medical procedure, for instance, receiving a manual command from the HC professional to terminate the medical procedure NV data file, detecting the end of a predetermined time period, or by failing to detect any motion in the surveillance area for a predetermined time period, or any combination of the sub-processes described above. With further regard to either retention format, the aim is to create documentation of a patient medical procedure as a stream of continuous surveillance data that can be easily identified as corresponding to a particular patient medical procedure.

In any case, it should be appreciated that exemplary nonvolatile memories 414 and 415 may be provided in various configurations, such as separate memory devices or partitions in a single memory. It should also be understood that camera control device 410 should have a nonvolatile memory for storing patient medical procedure NV data for future access. Optimally, primary memory 414 is a nonvolatile memory that is capable of retaining data in the event of a power loss. However, in accordance with other exemplary embodiments of the present invention, primary memory 414 may instead be configured as conventional RAM memory, wherein priority NV data is copied to a second nonvolatile memory immediately (such as secondary nonvolatile memory 415). While this configuration provides far less security for the priority surveillance NV data, utilizing RAM memory of nonvolatile flash memory is usually more economical. Additionally, a portion of nonvolatile primary memory 414 may be allocated for use by video processor 413. In this configuration, even surveillance data being processed by video processor 413 will be retained in the event of a power failure.

Surveillance system 420, including camera control device 410, along with its ancillary and peripheral components, is connect to a variety of physical locations (see FIG. 7), wherein the captured surveillance A/V data may be monitored, retained or otherwise processed for the HCF. Virtually every surveillance system 420 on HCF distribution network 440 will be connected to a patient monitoring sub-system for dedicated monitoring (depicted in the figure as patient monitoring sub-system 470 or nurses station). In accordance with one exemplary embodiment of the present invention, nurse monitor device 460 of patient monitoring sub-system 470 may be configured identically to camera control device 410. In that case, nurse monitor device 460 generally comprises processing unit 461 for storing and executing instructions, network controller 462 for connecting to HCF distribution network 440, video processor 463 and nonvolatile memories 464 and 465 for processing and/or displaying any captured surveillance data and/or patient medical procedure documentation screens. Video processor 463 may be integrated in a general purpose processing system or supplement the video processing capabilities of the general purpose processing system, which is coupled to video monitor 467 for viewing. Nurse monitor device 460 may also be coupled to a surveillance camera (not shown); in that case video processor 463 is also responsible for surveillance video captured as discussed above with regard to video processor 413. Because patient monitoring sub-system 470 may also be used as a supplemental input device for entering, editing or supplementing the information relating to a patient medical procedure, patient monitoring sub-system 470 is typically connected to a variety of data entry peripherals, such as manual interface device 469 (typically a mouse and/or keyboard) and/or touch screen video monitor 467.

FIG. 5A is a top view of a patient room with the present patient medical procedure documentation system in accordance with one exemplary embodiment of the present invention. Every patient room is required to have access to a lavatory, which is usually integrated in the room, for instance lavatory 506. Typically, patient room 400 comprises bed 502, furniture 504, lavatory 506, television 417 and a pillow speaker for listening to the television and calling the nurse (such as medical procedure/pillow speaker interface 300). Located in an optical position for viewing the area of patient room 400 containing the patient, usually the area including a surrounding bed 502, is surveillance system 420 (view angle 520 represents the aspect of video camera 416 which defines the surveillance area in patient room 400). Surveillance system 420 comprises at least video camera 416 and set top box 410 and is usually adjacent to television 417.

Figure 6A:
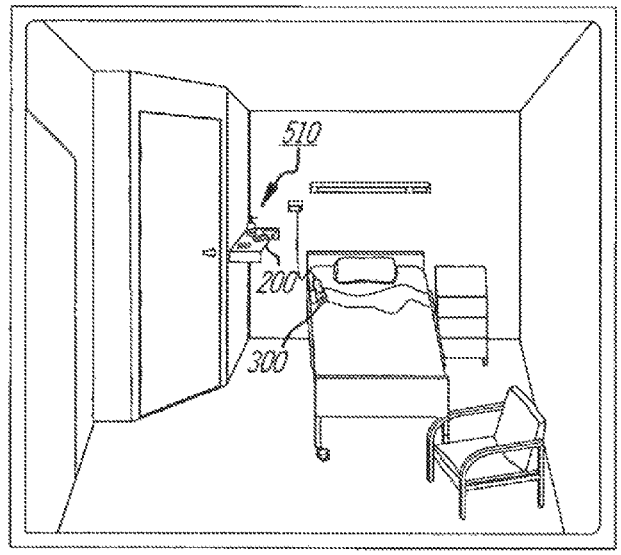
FIGS. 6A and 6B are diagrams showing the positioning of a hand cleaning/disinfectant station with a medical procedure remote in accordance with an exemplary embodiment of the present invention.
Figure 6B:
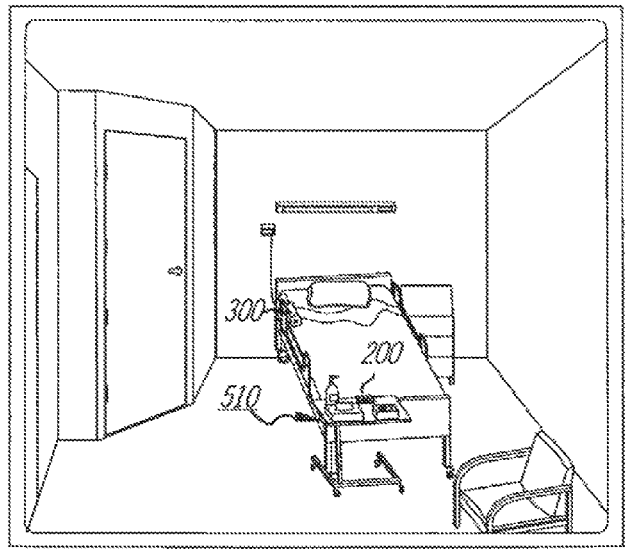

By law, any room in which a HC professional may come in physical contact with a patient must also include a hand washing/disinfectant station, depicted as hand cleaning/disinfectant station 510 in the figure and enlarged in FIG. 5B. At a minimum, hand cleaning/disinfectant station 510 will include germicidal disinfectant 512, protective gloves 514, wipes 516, usually on a station table 518, or the like, and a waste receptacle (not shown). Hand cleaning/disinfectant station 510 may be located in lavatory 506 or elsewhere in patient room 400. As depicted in FIG. 5A, hand cleaning/disinfectant station 510 occupies a mobile cart that may be repositioned throughout patient room 400 (here hand cleaning/disinfectant station 510 is at the foot of bed 502). Furthermore, and in accordance with one exemplary embodiment of the present invention, hand cleaning/disinfectant station 510 further comprises manual procedure remote 200. Placement of manual procedure remote 200 on or near station table 518 provides the HC professional with a means for initiating a medical procedure surveillance A/V file (or any other type of surveillance A/V file) during the disinfecting procedure (which must be performed prior to interacting with the patient). Notice in FIGS. 6A and 6B, hand cleaning/disinfectant station 510 is depicted as a mobile platform and fixed table adjacent to a wall, respectively.

In accordance with one aspect of the present invention, manual procedure remote 200 presents the HC professional with a relatively clean and uncomplicated interface; the HC professional merely actuates button 202 on manual procedure remote 200. Once actuated, manual procedure remote 200 sends patient medical procedure information to surveillance system 420 that initializes a patient medical procedure surveillance A/V file or other type of procedure surveillance A/V file. Alternatively, and in accordance with one exemplary embodiment of the present invention, the HC professional may also initiate a patient medical procedure surveillance A/V file using medical procedure/pillow speaker interface 300 or some other legacy interface device, such as a keyboard or tablet. It should be mentioned that manual procedure remote 200 contains at least one dedicated manual interface component for initiating a medical procedure surveillance A/V file; the HC professional may be required to interact with a procedure screen displayed on television 417 when initiating a medical procedure using legacy input devices and other interfaces without a dedicated procedure interface.

FIG. 7 is a diagram an HCF distribution network in which the present patient medical procedure documentation system may be implemented in accordance with an exemplary embodiment of the present invention. HCF distribution network 440 is coupled between patient rooms 400 and various HCF offices, such as nurses stations 450, patient administration 745 and system administration 748 via transmission medium 741 (such as twisted pair, coaxial conductor, power conductor, optical fiber, air or any other suitable transmission medium. Camera control device 410 is located in each patient room 400, as well as any other location that surveillance and/or monitoring is desired (such as nurse's station 450) and coupled through a variety of network switches 742 and other routing hardware. As mentioned, the present invention is flexible enough that for many applications, general purpose computer 710 (i.e., PC, laptop, handheld, palmtop, or other network device) may replace camera control device 410. If broadband access is required, HCF distribution network 440 may be connected to broadband connection 743 through network server/router/firewall 746. In practice, one or more servers may be connected to HCF distribution network 440, however at least one network storage, HCF network storage 744, should be provided for maintaining patient and other information, such as patient medical procedure A/V files.

Figure 8:
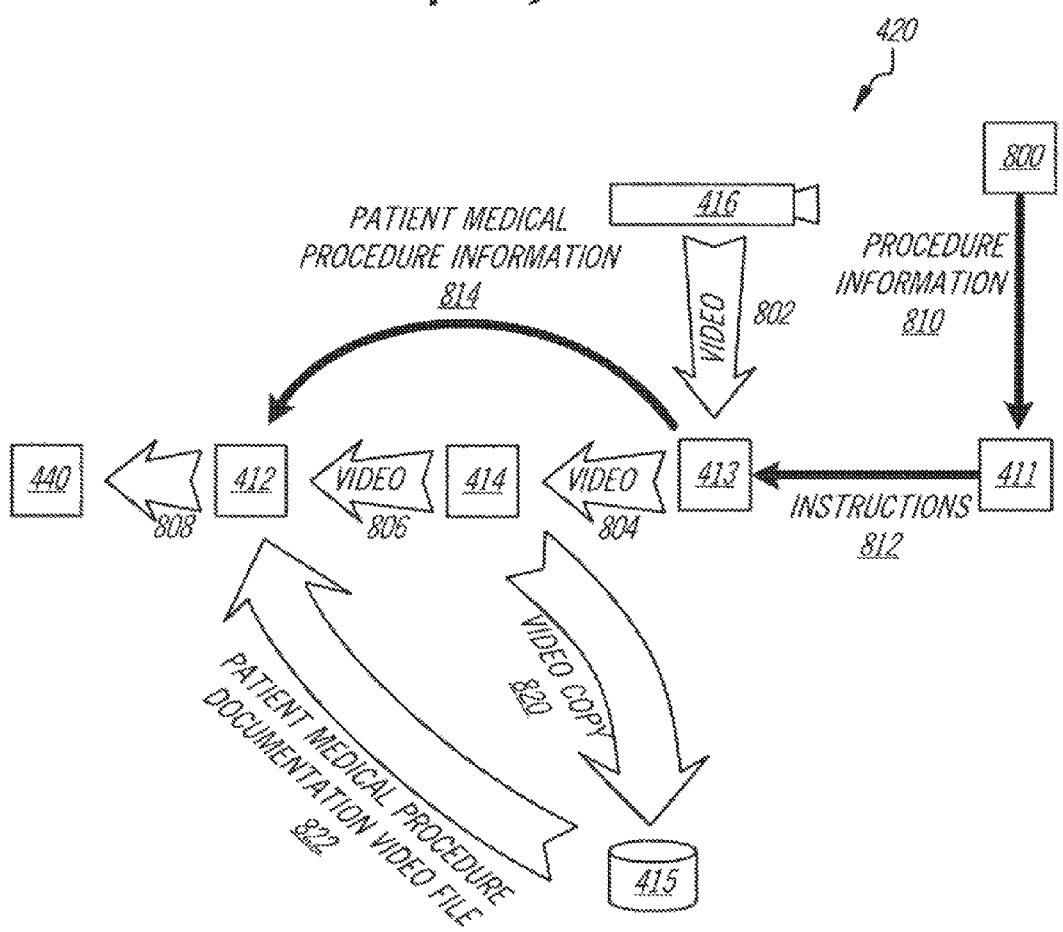
FIG. 8 is a logical diagram that illustrates the flow of surveillance video data across surveillance system 420 for documenting patient medical procedures in accordance with an exemplary embodiment of the present invention.

FIG. 8 is a logical diagram that illustrates the flow of surveillance video data across surveillance system 420 for documenting patient medical procedures in accordance with an exemplary embodiment of the present invention. The components of surveillance system 420 are essentially identical to those depicted in FIG. 4 with the exception of procedure remote interface 800. Interface 800 may be any manual or autonomous remote interface for sensing an event indicative of the commencement of a patient medical procedure, including but not limited to, manual procedure remote 200, medical procedure/pillow speaker interface 300, legacy interface device, transponder key FOB, RFID asset management, Bluetooth or the like. In operation, video camera 416 is continually capturing surveillance NV data from the surveillance area of the patient room. Video stream 802 is received at video processor 413, which processes the video data as required by service running at video processor 413 and/or processing unit 411. Processed video data 804 exits video processor 413 and is temporarily stored at primary nonvolatile memory 414. One reason for providing primary nonvolatile memory 414 is to provide a nonvolatile buffer for storing image frames prior to transmission across HCF distribution network 440. Network controller 412 arbitrates with HCF distribution network 440 for transmission bandwidth and passes transmission video 806 to network controller 412, which is, in turn, output to HCF network 440 as transmitted video 808. Transmitted video 808 may be monitored by anyone having the proper authorization and with access to HCF distribution network 440, and is typically recorded at a central database, such as a medical records database in network storage 744.

Primary nonvolatile memory 414 provides a temporary storage for processed video 804 during the arbitration and for temporary storage during high network usage periods and short-lived outages. The more surveillance video residing in primary nonvolatile memory 414, the greater the lag time between capturing the surveillance and receiving the video at a remote monitoring location. If adequate network bandwidth is not allocated to network controller 412, at some point network controller 412 will reduce the frame rate of video frames transmitted to HCF distribution network 440 by skipping every n frames residing in primary nonvolatile memory 414. Depending on the importance of the n frames in primary nonvolatile memory 414, processing unit 411 may instruct video processor 413 to save the video stream (or a portion of the video stream) in secondary memory 415. Hence, the present surveillance system reduces the likelihood of important surveillance data being overwritten (see copending U.S. patent application Ser. Nos. 10/735,307 and 12/151,452). However, this surveillance protocol does not guarantee that important NV data relating to patient medical procedures is available to document the medical procedure at a later time. Furthermore, even if the subject medical procedure happened to be saved, the medical record and billing administrator still must review a morass of surveillance video data for documentation for a specific procedure.

Therefore, in contrast to the flow of surveillance video data across surveillance system 420 discussed above, surveillance system 420 creates an alternate video path and protocol for handling surveillance video data that relates to a patient medical procedure (or any other procedure). Here, processor unit 411 receives procedure information 810 from procedure remote interface 800 and generates instructions for handling the upcoming video surveillance data. In accordance with one exemplary embodiment of the present invention, procedure remote interface 800 senses the presence of an HC professional and initiates a patient medical procedure A/V data file with the sensed information. Video processor 413 receives instructions 812 and immediately prioritizes any subsequent surveillance data, as well as surveillance data already retained in primary nonvolatile memory 414 over some predetermined time window. All prioritized medical procedure surveillance data 820 is copied to secondary nonvolatile memory 415. Prioritized medical procedure surveillance data 820 will remain in secondary nonvolatile memory 415 until it is overwritten by fresh medical procedure surveillance data. It should be mentioned that any medical procedure surveillance data 820 residing in secondary nonvolatile memory 415 may be de-prioritized remotely at any time by an authorized HCF administrator. Medical procedure surveillance data 820 provides that HCF with a safety copy of all patient medical procedures performed in the surveillance area. Once documentation of a patient medical procedure is available at HCF medical records database 744, the corresponding local safety copy of the patient procedure is no longer needed at secondary nonvolatile memory 415 and can be de-prioritized for overwriting, or expressly deleted.

Regardless of the existence of a safety copy of the medical procedure surveillance data 820 in secondary memory 415, the patient medical procedure surveillance data in primary memory 414 is forwarded onto HCF network 440 as transmitted video 808 from primary memory 414 as described above. Hence, transmitted video 808 that is also documentation of a patient medical procedure may simultaneously reside in network storage 744. The mere existence of this documentation of surveillance system 420, while important, does not substantially diminish the task of sorting video documentation of medical procedures from any other type of surveillance data.

Therefore, in accordance with still another exemplary embodiment of the present patient medical procedure documentation system, patient medical procedure surveillance video is identified as such and transmitted with the surveillance video sequences. Furthermore, status information concerning the subject patient medical procedure, i.e., that information sensed by local surveillance sub-system 420, is transmitted separately to the HCF administrators and billing professionals. This information provides the HCF administrators and billing professionals with the most complete and temporal information concerning a patient medical procedure. Returning to the diagram depicted in FIG. 8, procedure information contained in instructions 812 from processor unit 411 is stripped out and included in the file header(s) for the patient medical procedure surveillance data files. Typically, some or all information is coupled to each video frame prior to storing and/or transmitting (alternatively, the frame headers may contain a pointer to a location for the information). However, at some point before, during or after the patient medical procedure, a data file is transmitted to the network storage 744 containing all patient medical procedure information that was received at processor unit 411. The existence of this data file at network storage 744 provides valuable information that substantially reduces subsequent sort times for obtaining documentation for a patient medical procedure. Similarly, receipt of this information by the HCF administrators suggests that a surveillance record of a patient medical procedure exists at local surveillance sub-system 420 and, therefore, should be downloaded. At a minimum, the procedure information conveyed to the HCF administrators provides a network address of the source of the data and patient medical procedure information that was received at processor unit 411. With that information, HCF administrators can schedule a download of the corresponding patient medical surveillance video at local surveillance sub-system 420. There, processor unit 411 receives instructions for the HCF administrator to begin the download, which in turn authorizes the corresponding patient medical procedure documentation video file 822 to transfer across HCF distribution network 440, via network controller 412. Upon verification of the successful receipt of patient medical procedure documentation video file 822, the HCF administrator authorizes surveillance system 420 to de-prioritize or delete the corresponding surveillance file in secondary nonvolatile memory 415.

Figure 9A:
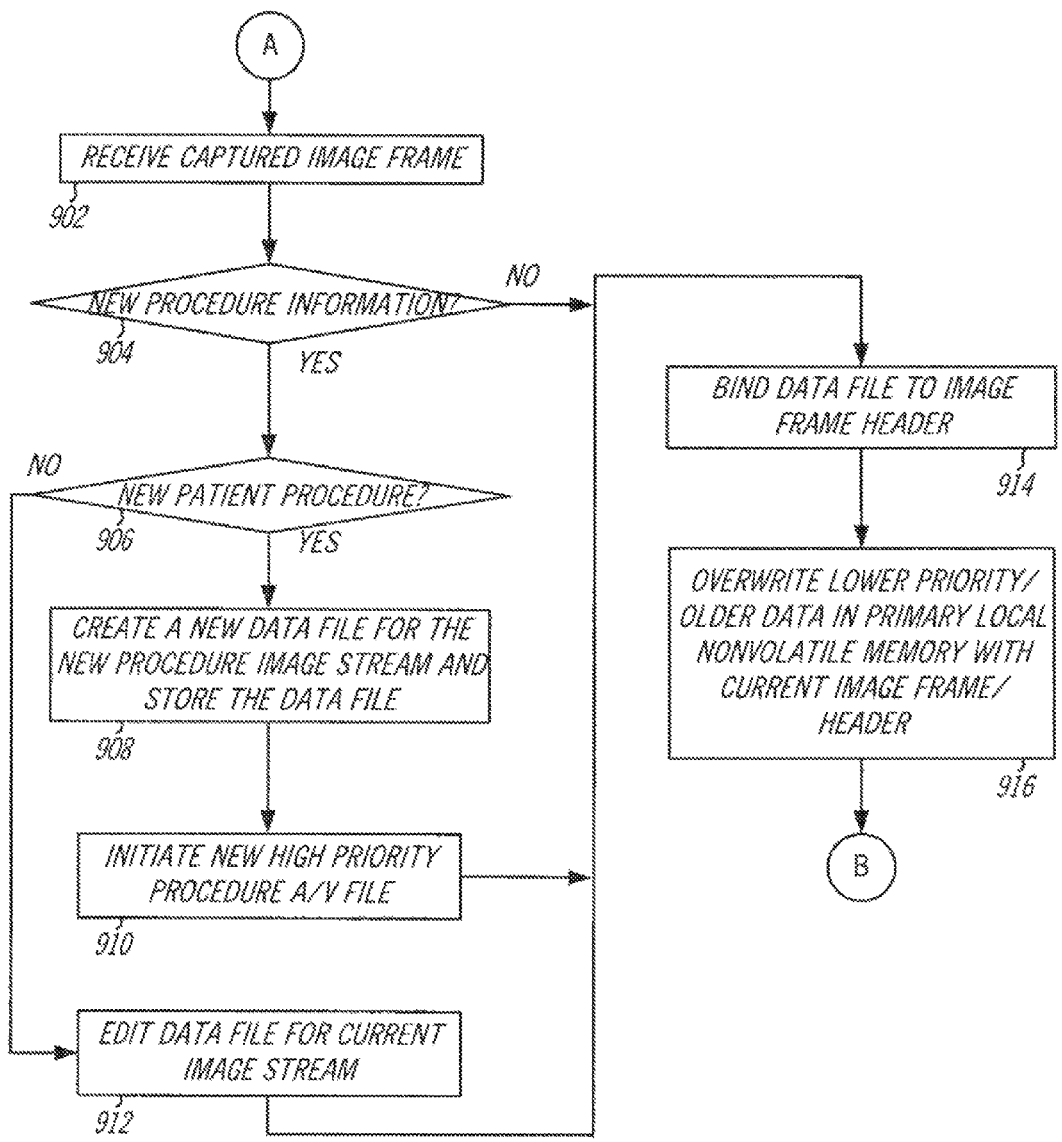
FIGS. 9A and 9B are a flowchart of a process for documenting patient medical procedures using a surveillance system in accordance with an exemplary embodiment of the present invention.
Figure 9B:
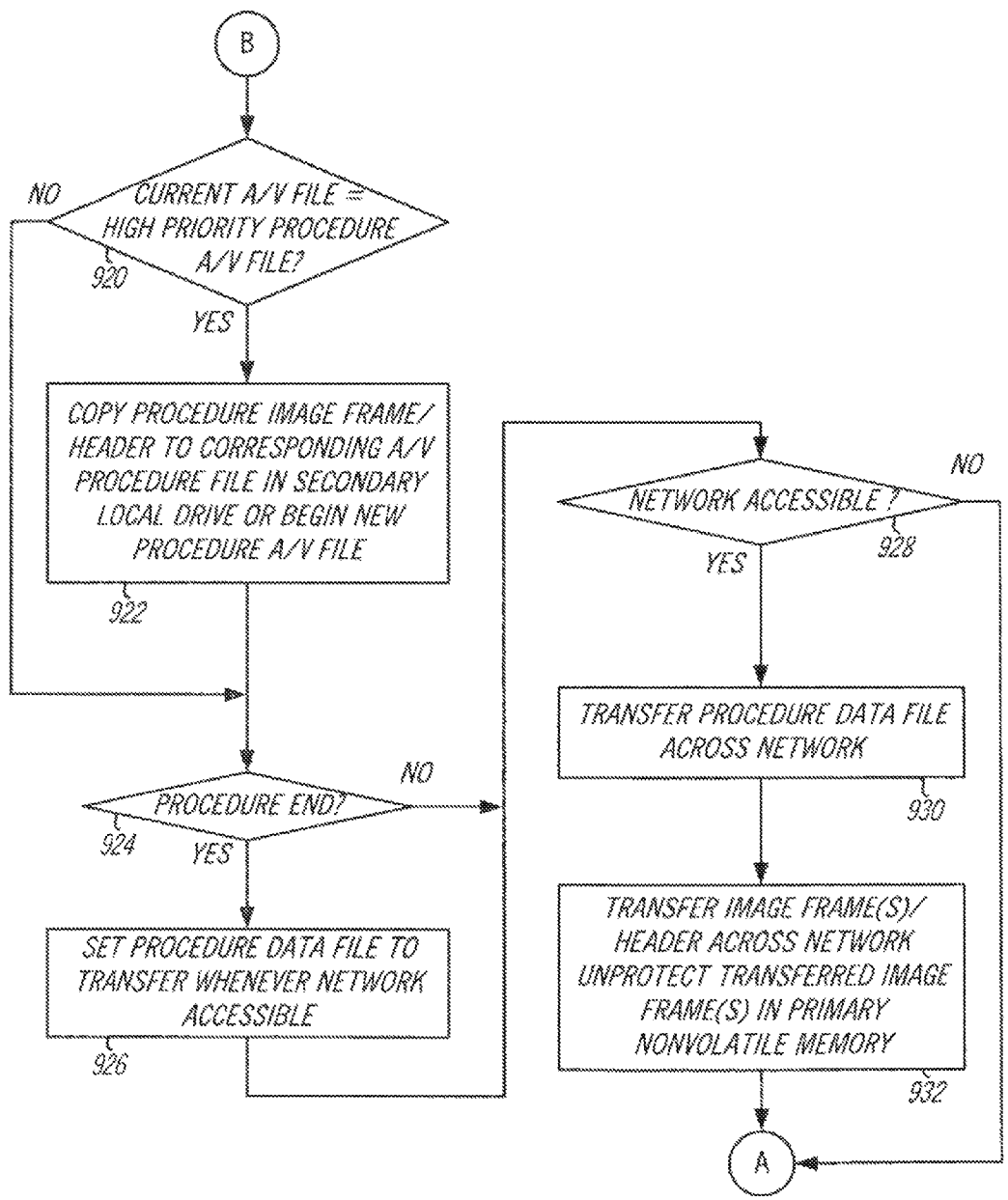

FIGS. 9A and 9B are a flowchart of a process for documenting patient medical procedures using a surveillance system in accordance with an exemplary embodiment of the present invention. Essentially, the present patient medical procedure documentation system involves operating the local surveillance sub-system in a predefined surveillance state, such as routine surveillance, motion-detected surveillance, procedure surveillance, medical procedure surveillance, etc. Surveillance data captured by the local surveillance sub-system are prioritized for storage in local memory and for transmission across HCF distribution network based on the current surveillance state of the local surveillance sub-system. One surveillance state of particular interest is defined for documenting patient medical procedures. When the local surveillance sub-system operates in this state, the captured surveillance data is prioritized and copied to a nonvolatile secondary memory for safety, in addition to the normal transmission over the HCF distribution network. The safety copy of the surveillance data stored in a secondary memory can be perused by any authorized HCF personnel and downloaded to a central HCF database during off-peak hours when network usage is low.

The present patient medical procedure documentation method is an iterative process which reiterates after each captured image frame is received at camera control device 410 (step 902). Initially, the system checks for any new information that may change the current surveillance state, modifies it, or provides supplemental information concerning the current surveillance state (step 904). This new procedure information may come from any of a variety of procedure remote interfaces, either local manual and autonomous sensing devices as discussed above. If no new procedure information has been received at local surveillance sub-system 420, the current procedure information is bound to the new captured image frame header (step 914) and that image frame overwrites lower priority and/or older data in the primary nonvolatile memory (step 916). Consecutive video image frames of the same type may be bound together in a single surveillance A/V file. The surveillance A/V file is then prioritized based on the type of surveillance data contained in the surveillance A/V file, for instance a routine surveillance file will have a very low priority, while surveillance data with motion detected will have a higher priority and patient medical procedure surveillance will also have a high priority. Newer and higher priority A/V surveillance data will take precedence over older and lower priority surveillance A/V data in the local memory.

Returning to step 904, if any new procedure information has been received subsequent to capturing the previous image frame that data should be tested to determine if the data is indicative of a new patient medical procedure or is supplemental information to an ongoing patient medical procedure (step 906). Typically, the present patient medical procedure documentation system operates in a patient procedure surveillance state or some other surveillance state having a lower priority. At the termination of one surveillance state, local surveillance sub-system 420 creates and transmits an end-of-procedure data file that signals the termination of the current patient procedure. The end-of-procedure data file contains the most temporal procedure data received by local surveillance sub-system 420. The end-of-procedure file may also contain a log of all procedure information received at the local surveillance device during the current patient procedure; this additional information increases search efficiency for a particular patient procedure.

It is sometimes difficult to determine whether or not a completely new medical procedure is to commence based solely on the procedure information received at camera control device 410 of local surveillance sub-system 420. For instance, if present patient medical procedure documentation system is operating in one patient procedure surveillance state and it senses the presence of a new HC professional in the surveillance area, there is a tendency to change patient procedure surveillance states, that is, to create a new patient procedure surveillance file based solely on the presence of the new HC professional in the surveillance area. The occurrence of this situation is more likely whenever a current patient procedure surveillance file is not manually terminated, but instead the present patient medical procedure documentation system relies on the expiration of a time period to terminate a patient procedure surveillance state (with or without sensing motion in the surveillance area). In this situation, the present patient medical procedure documentation system must either autonomously terminate the current patient procedure surveillance file and create a new patient procedure surveillance file for the new HC professional, or simultaneously write patient procedure files for two procedures (i.e., operate in two surveillance states simultaneously). Because memory space at the local surveillance sub-system is at a premium, duplicative surveillance A/V files cannot be permitted. A better solution is to simply include any newly sensed procedure information in the current procedure data file (and/or in the header of the current image frame). This may sometimes result in two different patient procedures being bound in the same patient surveillance A/V file. In that event, subsequent searches for either patient procedure can be resolved by the differences in the original procedure data and the supplemental procedure data, both sets of data may be included in all image frame headers subsequent to receiving the supplemental procedure data. Additionally, the end-of-procedure data file will usually contain a data log of all procedure events that were sensed during the patient procedure; that log will provide enough information to suggest the possibility of surveillance A/V data for two separate patient medical procedures.

In any case, if the new procedure information received by local surveillance sub-system 420 is merely supplemental procedure information, the current procedure data file retained in memory is modified with the new procedure data (step 912) and that data are bound to the frame header of the current image frame i.e., the newly captured image frame (step 914). At this point, the current image frame (and header information) overwrites lower priority and/or older data in the primary nonvolatile memory (step 916).

If, on the other hand, the newly received procedure information represents the commencement of an entirely new patient medical procedure (step 908), the present patient medical procedure documentation system creates a new procedure data file for the new procedure information (step 910) and then initiates a new procedure surveillance A/V file for the newly captured image frame and all subsequent frames until an end-of-procedure determination is made (step 910).

The new procedure surveillance A/V file is given a high priority to avoid inadvertent overwriting of the surveillance A/V data in the primary nonvolatile memory. Next, the new procedure data are bound to the frame header of the newly created image frame (step 914) and the newly created image frame and header information overwrites lower priority and/or older data in the primary nonvolatile memory (step 916).

Next, the present patient medical procedure documentation system tests the current A/V file to determine if it is a high priority procedure surveillance A/V file (step 920). If the file is confirmed to be a high priority procedure surveillance A/V file, the current image frame and header information is copied to the corresponding procedure surveillance A/V file open in the secondary Memory (step 922). If the current image frame if the first frame for a new patient procedure, then the present patient medical procedure documentation system creates a new procedure surveillance A/V file in the secondary memory and copies the current image frame and header information to that file.

At some point, the present patient medical procedure documentation system will detect an event that signals the end of the ongoing patient procedure (step 924), for instance local surveillance sub-system 420 receives a manual termination request from the HC professional present for the procedure or a predetermined time period expires. If the patient procedure has not ended, the process invokes a network transmission routine (see steps 928-932 discussed below). Alternatively, if the present patient medical procedure documentation system detects the end of the patient procedure, an end-of-procedure data file is created that will be sent to the HCF medical records and billing administrators at the first opportunity HCF distribution network 440 is accessible (step 926). The end-of-procedure file is of particular importance as it contains an event log of all procedure events that occurred during the patient procedure. The end-of-procedure file also alerts the HCF medical records and billing administrators to the presence of a surveillance A/V file stored in the secondary memory of local surveillance sub-system 420. With this information, the patient billing professionals can schedule download of procedure surveillance A/V data that documents the corresponding patient medical procedure.

Next, a network transmission routine is invoked for transmitting the current image frame over distribution network 440. Initially, network controller 412 attempts to access the HCF distribution network (step 928). If the network is unavailable, the process reverts to step 902 for receiving another captured image frame. Because both the current image frame and any new procedure information are temporarily stored in the primary nonvolatile memory, those files can be transmitted in the next iteration of the process. Hence, once the network is accessible to local surveillance sub-system 420, any new procedure data files are transferred (step 930) as well as all image frames and their corresponding headers (step 932). It should be mentioned that between data transfers network controller 412 checks the backlog in the primary memory. If a bottleneck of surveillance image data is occurring, the controller will invoke a transfer method to reduce lag time, such as lower the frame transfer rate, or merely skipping a group of lower priority image frames. In either case, network controller 412 may make a temporary local copy of the surveillance file that can be accessed by HC professionals at monitoring sub-system 460.

Figure 10:
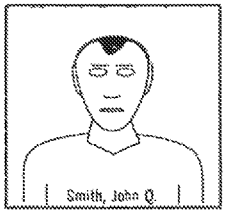
FIG. 10 is an illustration of a patient procedure screen for the present patient medical procedure documentation system that may be accessed by authorized HC professionals in accordance with an exemplary embodiment of the present invention.

FIG. 10 is an illustration of a patient procedure screen for the present patient medical procedure documentation system that may be accessed by authorized HC professionals in accordance with an exemplary embodiment of the present invention. Initially, it should be mentioned that some or all of procedure form 1000 may be displayed and completed beforehand by the HCF processional performing the patient procedure or any other authorized HCF processional (such as a nurse or other HCF administrator). Upon scheduling a patient procedure, procedure form 1000 is generated at a remote location, for instance nurse station 450, and includes all of available information related to the patient procedure, e.g., at least the patient information 1010 and procedure information 1030, i.e., procedure name, billing code, etc. The entry fields of procedure form 1000 are completed by the HC professional using a PC, tablet, nurse monitor device 460 or any other device connected to HCF distribution network 440. Alternatively, present patient medical procedure documentation system generates procedure form 1000 at the local surveillance area, such as patient room 400, either in response to a manual interaction from a HC professional (for instance by using procedure remote 200, medical procedure/pillow speaker interface 300 or a legacy input device in communication with camera control device 410 of local surveillance sub-system 420) or autonomously (for instance by the camera control device 410 of local surveillance sub-system 420 sensing the presence of an HC professional within the range of medical procedure remote interface 418). Procedure form 1000 contains a log of all patient procedure information that will be included in the end-of-procedure file. Recall that the end-of-procedure file is transmitted at the conclusion of the patient procedure. Many of the entry fields in procedure form 1000 may be entered, edited or sublimated at the local surveillance area using medical procedure/pillow speaker interface 300 or some other legacy interface device, such as a keyboard or tablet that is in communication with local surveillance sub-system 420. Optimally, the present patient medical procedure documentation system automatically completes as many fields as possible in order to reduce the workload on the HC professional performing the patient procedure.

Whether procedure form 1000 is filled automatically or manually, the form is largely auto-fill, wherein the system recognizes certain inputted information and then auto-fills all related entry fields. For example, in response to a patient name being entered, the present patient medical procedure documentation system brings up and fills in the remainder of patient information 1010. Information for Date/Time/Room fields 1020 is provided by local surveillance sub-system 420 and the entry fields may be un-editable to HC professionals.

One aim of procedure form 1000 is to provide a simplified page for entering patient procedure information. In practice, a new procedure form will be automatically created for each instance that local surveillance sub-system 420 senses the presence of a HC professional. For example, notice from the content of auto detection field 1040 that local surveillance sub-system 420 has detected the presence of McKinney (FOB 0421), Jones (FOB 9101) and Henderson (FOB 2211). Here, receiver/interrogator and medical procedure remote interface 418 has detected three FOBs within its range and interrogated them to produce the identities of their owners and their positions in the HCF. In response, the present patient medical procedure documentation system generates a new procedure form 1000 in anticipation of an upcoming patient medical procedure.

In certain situations, the present patient medical procedure documentation system will generate a bogus procedure form 1000 that does not document any patient medical procedure merely due to the presence of HC professionals being detected within the range of medical procedure remote interface 418. The surveillance A/V files that do not correlate to a procedure are eventually discarded by the HCF medical records and patient billing professionals. Some of these bogus surveillance A/V files can be identified as such by the HC professional present in the surveillance area. Notice directly to the right of the HC professional identities in the procedure form 1000 is an entry field for each of the HC professional's duty or status for the current patient procedure. In the example procedure form, McKinney is listed as the Primary attending in charge of the patient medical procedure and Jones is listed as a Witness to the procedure. Notice however, that Henderson has been detected by receiver/interrogator and medical procedure remote interface 418, but is not actually present for the procedure. Medical procedure remote interface 418 detects any HC professionals within its range, so any HC professionals that are detected but not present must be documented on procedure form 1000. Hence, the procedure information for any bogus surveillance A/V files wherein an HC professional is not in the surveillance area can be amended to show that the detected professional is Not Present. Conversely, manual entry fields 1050 are provided for manually entering any HC professionals that are present in the surveillance area but not detected by medical procedure remote interface 418.

With further attention to procedure form 1000, procedure information fields 1030 identify the patient procedure being performed sufficiently for identifying any documentation to the procedure, such as a corresponding surveillance A/V data file. Information for procedure information fields 1030 must be entered manually, however, may be empty. In that case, the HCF medical records and patient billing professionals must identify the patient procedure that correlates to the particular documentation surveillance A/V file. This process is greatly aided by the receipt of an end-of-procedure data file that is generated by the present patient medical procedure documentation system at the conclusion of a procedure.

Figure 11:
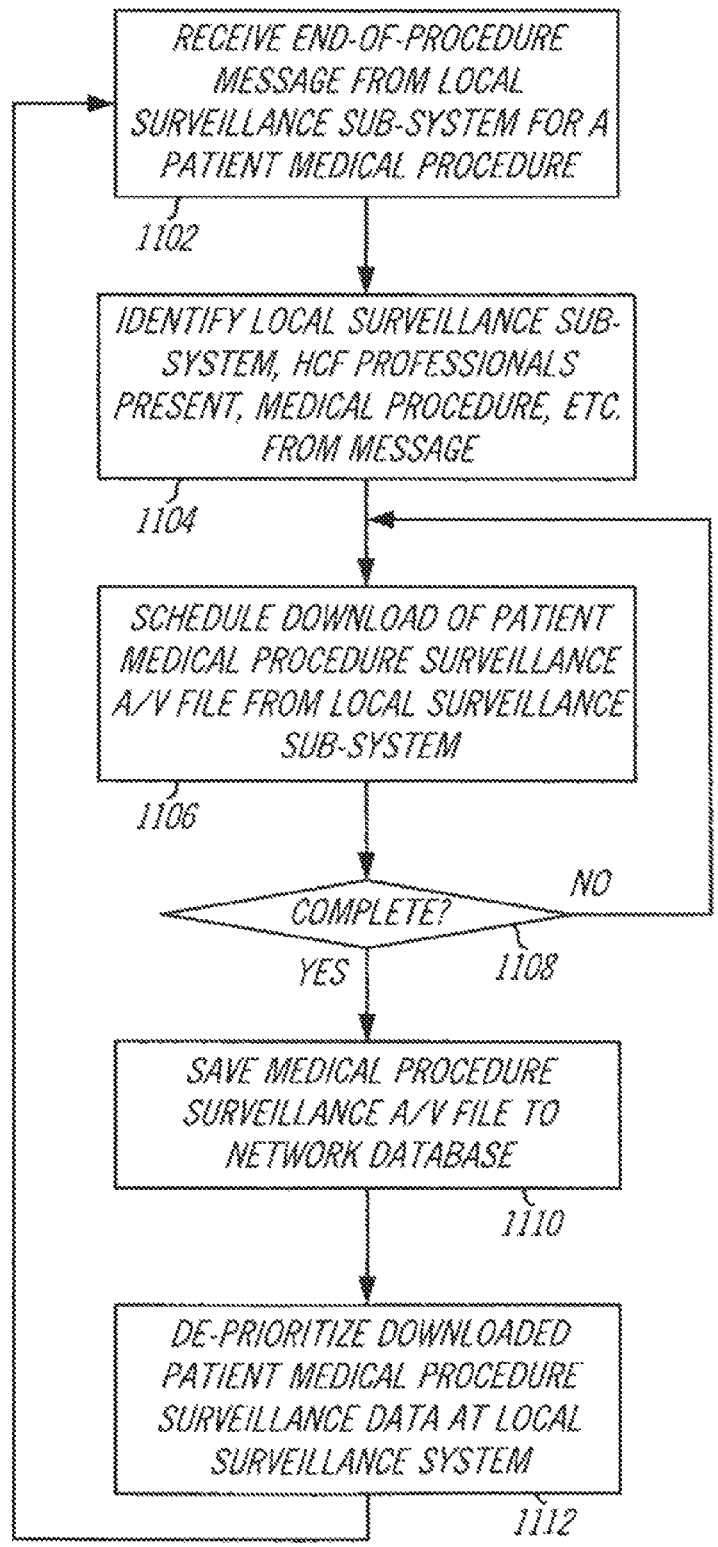
FIG. 11 is a flowchart of a process for collecting the documentation surveillance A/V files corresponding to a patient medical procedure in accordance with an exemplary embodiment of the present invention.

FIG. 11 is a flowchart of a process for collecting the documentation surveillance A/V files corresponding to a patient medical procedure in accordance with an exemplary embodiment of the present invention. Recall that immediately upon local surveillance sub-system 420 sensing the presence of a HC professional, a copy of subsequently captured surveillance A/V data is copied to secondary nonvolatile memory 415 for safety. Local surveillance sub-system 420 transmits an end-of-procedure data file across HCF distribution network 440 once the patient medical procedure is terminated. The present method is an iterative process running on a HCF network device, such as HCF network server 746, that constantly listen for end-of-procedure messages on HCF distribution network 440. When HCF network server 746 receives an end-of-procedure message (step 1102), the present patient medical procedure documentation system opens the message for the identity of the local surveillance sub-system that generated the file and reads any other patient procedure data that may be present in the end-of-procedure message, such as the identities of HC professionals present, information concerning the patient medical procedure, patient information, etc. (step 1104). The end-of-procedure message will typically also identify the corresponding documentation surveillance A/V file with a unique file identifier. With this information, the present patient medical procedure documentation system can either attempt to immediately download the corresponding patient surveillance A/V file from the particular local surveillance sub-system 420 or schedule a download attempt in the future (step 1106). It is expected that during regular business hours, HCF distribution network 440 may not have sufficient bandwidth to support downloads of multiple documentation surveillance A/V files and, therefore, the present patient medical procedure documentation system schedules all download attempts for nonpeak hours. If one attempt to retrieve a documentation surveillance A/V file fails, (step 1108) the process reverts to step 1106 and a subsequent download time is scheduled. If at step 1108, the documentation surveillance A/V file is successfully downloaded to HCF network server 746 from local surveillance sub-system 420, the documentation surveillance A/V file is stored to an HCF network device, such as HCF network storage 744 (step 1110). The copy of the surveillance A/V file residing in local surveillance sub-system 420 is de-prioritized in memory, thereby freeing up memory space in secondary nonvolatile memory 415 for higher priority data (step 1112).

Any time a patient's medical procedure requires further documentation, i.e., for patient billing, routine monitoring of performance of HC professionals, etc., a copy of the corresponding patient procedure surveillance A/V file should be present in a centralized location in the HCF, such as HCF network storage 744. Documentation for the patient procedures can be accessed at will. FIG. 12 is a flowchart illustrating a process for documenting patient medical procedures using surveillance A/V files corresponding to the patient medical procedure in accordance with an exemplary embodiment of the present invention. The process begins with the present patient medical procedure documentation system receiving a request for documentation of a patient medical procedure (step 1202). Typically, the request identifies both the patient and the procedure and usually the date that the procedure was performed and the attending HC professional(s) (step 1204). Using the patient name, procedure identification, date and attending HC professional(s), the HCF database is queried for the documentation (step 1206). If a surveillance A/V file exists in the HCF database for the procedure, documentation is created for the request (step 1226). The documentation is usually in the form of an A/V file that is appended to the request, but might instead be only a link or address to the file on the HCF database. As discussed above, not all surveillance A/V files contain all of the procedure information contained in the request, hence, fulfilling the request may require some review by an HCF administrator. At a minimum, every surveillance A/V file will contain the patient name and room number, and the identity of at least one HC professional. Therefore, if at step 1208, a surveillance A/V is not returned that correlates to the request data, the database may be queried by patient and date for all procedure surveillance A/V files (step 1210). Those files are reviewed by an HC professional of the subject of the request. If the requested patient procedure is identified, the process reverts to step 1226 and documentation for the patient procedure is created. If not, the search of the HCF database is broadened for a search for all surveillance A/V files for all procedures performed on the subject patient (step 1214). This requires substantially more review by the HC professional, but much less than search all surveillance data for the patient. If the file exists (step 1216), the process reverts to step 1226 and documentation for the patient procedure is created. If no documentation for the procedure can be identified from the HCF database, it is possible that the surveillance A/V file is present at the local surveillance sub-system. In that case, the patient name and room number at the date of the procedure is gathered (step 1218) because the documentation file may still exist on the secondary nonvolatile memory of the local surveillance sub-system for the patient room. The local surveillance sub-system 420 is accessed for the surveillance A/V file (step 1220) and if it exists locally (step 1222) the process reverts to step 1226 and documentation for the patient procedure is created. A copy is also retained at the HCF database. If no documentation can be identified, an error is returned and the HC professionals begin the task of searching all surveillance data associated with the identified patient.

The exemplary embodiments described below were selected and described in order to best explain the principles of the invention and the practical application, and to enable others of ordinary skill in the art to understand the invention for various embodiments with various modifications as are suited to the particular use contemplated. The particular embodiments described below are in no way intended to limit the scope of the present invention as it may be practiced in a variety of variations and environments without departing from the scope and intent of the invention. Thus, the present invention is not intended to be limited to the embodiment shown, but is to be accorded the widest scope consistent with the principles and features described herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

I claim:

1. A surveillance system for documenting patient procedures comprising:
   a surveillance camera for capturing a plurality of video frames of a surveillance area;
   a patient procedure remote for detecting a presence of a health care professional proximate to the surveillance area to perform a patient procedure; and
   a control system comprising memory and at least one processing unit, the control system configured to:
      receive the plurality of video frames from the surveillance camera;
      receive an indication of the presence of the healthcare professional proximate to the surveillance area from the patient procedure remote;
      create a medical procedure data file based on the reception of the indication, the medical procedure data file containing location information, timestamp information, an identity of the healthcare professional, and at least some of the plurality of video frames showing the patient procedure; and
      save the medical procedure data file in the memory.

2. The surveillance system of claim 1, further comprising a station, the station configured to:
   search the memory based on one or more of the identity of the patient, the location information, and the identity of the healthcare professional;
   retrieve the medical procedure data file based on the search; and
   display the at least some of the plurality of video frames showing the patient procedure.

3. The surveillance system of claim 1, wherein the patient procedure remote is configured to receive a manually input indication of the type of the medical procedure, and the medical procedure data file contains an indication of the type of the medical procedure based on the manually input indication.

4. The surveillance system of claim 1, wherein the control system is configured to prioritize the medical procedure data file relative to routine surveillance files.

5. The surveillance system of claim 4, wherein the prioritization of the medical procedure data file relative to the routine surveillance files protects the medical procedure data file from overwriting while allowing the routine surveillance files to be overwritten.

6. The surveillance system of claim 1, wherein the patient procedure remote comprises a personal identification device configured for wireless interrogation for detecting the presence of the healthcare professional.

7. The surveillance system of claim 1, wherein the patient procedure remote comprises an interface device configured to generate the indication of the presence of the healthcare professional based on a manual input on the interface device from the healthcare professional.

8. The surveillance system of claim 7, wherein the interface device comprises at least one of a switch, a lever, a knob, a button, a mouse, a pointer, a trackball, a keyboard, a touchpad, and a touch screen.

9. The surveillance system of claim 1, wherein the control system is configured to determine a beginning of the patient procedure and an end of the patient procedure, and the at least some of the plurality of video frames are captured between the beginning of the patient procedure and the end of the patient procedure.

10. The surveillance system of claim 1, wherein the control system comprises one or more coordinating devices.

11. A method of operating a surveillance system to document patient procedures, the surveillance system comprising a surveillance camera, a medical procedure remote device, memory, and at least one processing unit, the method comprising: capturing a plurality of video frames of a surveillance area with the surveillance camera; the medical procedure remote device detecting a presence of a health care professional proximate to the surveillance area to perform a patient procedure; creating a medical procedure data file based on the detection of the presence of the health care professional, the medical procedure data file containing location information, timestamp information, an identity of the healthcare professional, and at least some of the plurality of video frames showing the patient procedure; and saving the medical procedure data file in the memory, wherein detecting, creating, and saving are performed by the at least one processing unit.

12. The method of claim 11, further comprising:
   searching the memory based on one or more of the identity of the patient, the location information, and the identity of the healthcare professional;
   retrieving the medical procedure data file based on the search; and displaying the at least some of the plurality of video frames showing the patient procedure on a screen.

13. The method of claim 11, further comprising receiving a manually input indication of the type of the medical procedure on the medical procedure remote, wherein the medical procedure data file contains an indication of the type of the medical procedure based on the manually input indication.

14. The method of claim 11, further comprising prioritizing the medical procedure data file relative to routine surveillance files.

15. The method of claim 14, further comprising overwriting the routine surveillance files while not overwriting the medical procedure data file based on the prioritization of the medical procedure data file.

16. The method of claim 11, wherein detecting the presence of the health care professional comprises interrogating a personal identification device.

17. The method of claim 11, further comprising receiving a manual input on the interface device from the healthcare professional, wherein the detection of the presence of the health care professional is based on the reception of the manual input.

18. The method of claim 17, wherein the interface device comprises at least one of a switch, a lever, a knob, a button, a mouse, a pointer, a trackball, a keyboard, a touchpad, and a touch screen.

19. The method of claim 11, further comprising determining a beginning of the patient procedure and an end of the patient procedure, wherein the at least some of the plurality of video frames are captured between the beginning of the patient procedure and the end of the patient procedure.

20. The surveillance system of claim 1, wherein the identity of the healthcare professional comprises at least one of a job title, a description, a position, a name, and an employee number.

* * * * *